(12) United States Patent
Hovinen et al.

(10) Patent No.: US 8,143,057 B2
(45) Date of Patent: Mar. 27, 2012

(54) CHELATING AGENTS AND HIGHLY LUMINESCENT AND STABLE CHELATES AND THEIR USE

(75) Inventors: Jari Hovinen, Raisio (FI); Veli-Matti Mukkala, Kaarina (FI); Harri Hakala, Turku (FI); Jari Peuralahti, Turku (FI)

(73) Assignee: Wallac Oy, Turku (FI)

( * ) Notice: Subject to any disclaimer, the term of this patent is extended or adjusted under 35 U.S.C. 154(b) by 71 days.

(21) Appl. No.: 12/580,990

(22) Filed: Oct. 16, 2009

(65) Prior Publication Data

US 2010/0036102 A1 Feb. 11, 2010

Related U.S. Application Data

(62) Division of application No. 11/004,061, filed on Dec. 6, 2004, now Pat. No. 7,625,930.

(60) Provisional application No. 60/531,016, filed on Dec. 22, 2003.

(30) Foreign Application Priority Data

Dec. 18, 2003 (FI) ..................................... 20031858

(51) Int. Cl.
*C07D 401/02* (2006.01)
*A61K 31/44* (2006.01)

(52) U.S. Cl. ........ 435/332; 514/269; 514/333; 546/255; 546/256; 544/123

(58) Field of Classification Search .......................... None
See application file for complete search history.

(56) References Cited

U.S. PATENT DOCUMENTS

| | | |
|---|---|---|
| 4,761,481 A | 8/1988 | Hale et al. |
| 4,925,804 A | 5/1990 | Hale et al. |
| 5,032,677 A | 7/1991 | Hale et al. |

FOREIGN PATENT DOCUMENTS

| | | |
|---|---|---|
| WO | WO 89/08263 | 9/1989 |
| WO | WO 90/00550 | 1/1990 |
| WO | WO 97/40055 | 10/1997 |
| WO | WO 2008/020113 | 2/2008 |

OTHER PUBLICATIONS

McNaught et al., *International Union of Pure and Applied Chemistry, Compendium of Chemical Terminology, IUPAC Recommendations*, Second Edition, p. 68, 1997.
Latva et al., "Correlation between the lowest triplet state energy level of the ligand and lanthanide(III) luminescence quantum yield," *Journal of Luminescence*, 1997, vol. 75, pp. 149-169, Elsevier Science B.V., England.
Mukkala et al., "New fluorescent Eu(III) and Tb(III) chelates of 2,2'-bipyridine derivatives," *Eur. J. Solid Statelnorg. Chem.*, 1992, vol. 29, pp. 53-56, Wiley-VCH Verlag GmbH & Co. KGaA, Germany.
Mukkala et al., "Development of Luminescent Europium (III) and Terbium (III) Chelates of 2,2': 6',2"—Terpyridine Derivatives for Protein Labelling," *Helvetica Chimica Acta*, 1993, vol. 76, pp. 1361-1378, Wiley-VCH Verlag GmbH & Co. KGaA, Germany.
Mukkala et al., "New 2,2'-Bipyridine Derivatives and Their Luminescence Properties with Europium(III) and Terbium(III) Ions," *Helvetica Chimica Acta*, 1992, vol. 75, pp. 1578-1592, Wiley-VCH Verlag GmbH & Co. KGaA, Germany.
Rao et al., *Journal of the American Chemical Society*, 1963, vol. 85, No. 16, pp. 2532-2533, The American Chemical Society, Washington, D.C.

*Primary Examiner* — Zinna Northington Davis
(74) *Attorney, Agent, or Firm* — Buchanan Ingersoll & Rooney PC

(57) ABSTRACT

This invention relates to a group of novel chelating agents, novel chelates, biomolecules labeled with said chelates or chelating agents as well as solid supports conjugated with said chelates, chelating agents or labeled biomolecules. Especially the invention relates to novel chelating agents useful in solid phase synthesis of oligonucleotides or oligopeptides and the oligonucleotides and oligopeptides so obtained.

3 Claims, No Drawings

CHELATING AGENTS AND HIGHLY LUMINESCENT AND STABLE CHELATES AND THEIR USE

CONTINUING DATA

This application is a DIV of Ser. No. 11/004,061 filed Dec. 6, 2004 which is U.S. Pat. No. 7,625,930 which claims benefit of 60/531,016 filed Dec. 22, 2003.

FIELD OF THE INVENTION

This invention relates to a group of novel chelating agents, novel chelates, biomolecules labeled with said chelates or chelating agents as well as solid supports conjugated with said chelates, chelating agents or labeled biomolecules.

BACKGROUND OF THE INVENTION

The publications and other materials used herein to illuminate the background of the invention, and in particular, cases to provide additional details respecting the practice, are incorporated by reference.

Because of their unique luminescence properties lanthanide(III) chelates are often used as non-radioactive markers in a wide variety of routine and research applications. Since lanthanide(III) chelates give strong, long decay-time luminescence, they are ideal labels for assays where high sensitivity is required. Time-resolved fluorometric assays based on lanthanide chelates have found increasing applications in diagnostics, research and high throughput screening. The heterogeneous DELFIA® technique is applied in assays requiring exceptional sensitivity, robustness and multi-label approach [Hemmilä et al. *Anal. Biochem.* 1984, 137, 335-343]. Development of highly luminescent stable chelates extends the use of time resolution to homogeneous assays, based on fluorescence resonance energy transfer (TR-FRET), fluorescence quenching (TR-FQA) or changes in luminescence properties of a chelate during a binding reaction [Hemmilä, I.; Mukkala, V.-M. *Crit. Rev. Clin. Lab. Sci.* 2001, 38, 441-519].

Most commonly the conjugation reaction is performed in solution between an amino or mercapto group of a bioactive molecule (such as protein, peptide, nucleic acid, oligonucleotide or hapten) and isothiocyanato, haloacetyl, 3,5-dichloro-2,4,6-triazinyl derivatives of lanthanide(III) chelates, as well as other reporter groups. Since in all the cases the labeling reaction is performed with an excess of an activated label, laborious purification procedures cannot be avoided. Especially, when attachment of several label molecules, or site-specific labeling in the presence of several functional groups of similar reactivities is required, the isolation and characterization of the desired biomolecule conjugate is extremely difficult, and often practically impossible. Naturally, solution phase labeling of large biomolecules, such as proteins cannot be avoided. In these cases, the labeling reaction has to be as selective and effective as possible.

A number of attempts have been made to develop new highly luminescent chelate labels suitable for time-resolved fluorometric applications. These include e.g. stabile chelates composed of derivatives of pyridines [U.S. Pat. Nos. 4,920, 195, 4,801,722, 4,761,481, PCT/FI91/00373, U.S. Pat. No. 4,459,186, EP A-0770610, Remuinan et al, *J. Chem. Soc. Perkin Trans* 2, 1993, 1099], bipyridines [U.S. Pat. No. 5,216, 134], terpyridines [U.S. Pat. Nos. 4,859,777, 5,202,423, 5,324,825] or various phenolic compounds [U.S. Pat. No. 4,670,572, U.S. Pat. No. 4,794,191, Ital Pat. 42508 A789] as the energy mediating groups and polycarboxylic acids as chelating parts. In addition, various dicarboxylate derivatives [U.S. Pat. Nos. 5,032,677, 5,055,578, 4,772,563] macrocyclic cryptates [U.S. Pat. No. 4,927,923, WO 93/5049, EP-A-493745] and macrocyclic Schiff bases [EP-A-369-000] have been disclosed. Also a method for the labeling of biospecific binding reactant such as hapten, a peptide, a receptor ligand, a drug or PNA oligomer with luminescent labels by using solid-phase synthesis has been published [U.S. Pat. No. 6,080,839]. Similar strategy has also been exploited in multilabeling of oligonucleotides on solid phase [EP A 1152010, EP A 1308452].

Although fluorescent rare earth chelates comprising arylpyridine diacid and aryl substituted 2,6-bis[N,N-di(carboxyalkyl)aminoalkyl]pyridine moieties have been published [Hemmilä et al., *J Biochem Biophys Methods* 26; 283-90 (1993); U.S. Pat. No. 4,761,481] the chelates or chelating agents described in the present invention herein have not been disclosed before.

OBJECTS AND SUMMARY OF THE INVENTION

The main object of the present invention is to provide chelating agents and metal chelates thereof, useful for labeling biomolecules, for use as probes in time-resolved fluorescence spectroscopy, magnetic resonance imaging (MRI) or positron emission tomography (PET).

A particular object of this invention is to provide a chelating agent which gives a very strong fluorescense with different chelated lanthanide ions, particularly with europium (III), samarium (III), terbium (III) and dysprosium (III). Such lanthanide chelates are especially useful in multiparameter bioaffinity assays and in high-throughput screening of drug candidates.

A further object of this invention is to provide chelating agents giving rise to metal chelates of high stability. A particular object is to achieve chelates with strong stability enough for use in in vivo applications, for example in MRI or PET applications.

A further object is to provide chelates or chelating agents suitable for labeling of biomolecules as such in solution.

Yet another object is to provide chelates suitable for labeling oligopeptides or oligonucleotides simultaneously with their synthesis on a solid phase.

Yet another object is to provide a solid support conjugated with chelates, chelating agents or biomolecules according to this invention.

Thus, according to one aspect this invention concerns a chelating agent comprising
- a chromophoric moiety comprising two or more aromatic units, wherein at least one of the aromatic units is a trialkoxyphenylpyridyl group, where the alkoxy groups are the same or different, and the pyridyl groups are i) tethered directly to each other to form a bipyridyl or terpyridyl group, respectively, or ii) tethered to each other via N-containing hydrocarbon chains,
- a chelating part comprising at least two carboxylic acid or phosphonic acid groups, or esters or salts of said acids, attached to an aromatic unit of the chromophoric moiety, either directly or via an N-containing hydrocarbon chain, and
- optionally a reactive group A, tethered to the chromophoric moiety or to the chelating part either directly or via a linker x, said reactive group A enabling binding to a biomolecule or to a functional group on a solid phase.

According to another aspect, the invention concerns a chelate comprising
- a metal ion,
- a chromophoric moiety comprising two or more aromatic units, wherein at least one of the aromatic units is a trialkoxyphenyl pyridyl group, where the alkoxy groups are the same or different, and the pyridyl groups are i) tethered directly to each other to form a bipyridyl or terpyridyl group, respectively, or ii) tethered to each other via N-containing hydrocarbon chains,
- a chelating part comprising at least two carboxylic acid or phosphonic acid groups, or esters or salts of said acids, attached to an aromatic unit of the chromophoric moiety, either directly or via an N-containing hydrocarbon chain, and
- optionally a reactive group A, tethered to the chromophoric moiety or to the chelating part either directly or via a linker x, said reactive group A enabling binding to a biomolecule or to a functional group on a solid phase.

According to a third aspect, the invention concerns a biomolecule conjugated with a chelate according to this invention.

According to a fourth aspect, the invention concerns a biomolecule conjugated with a chelating agent according to this invention.

According to a fifth aspect, the invention concerns a solid support conjugated with a chelate or a labeled biomolecule according to this invention.

According to a sixth aspect, this invention concerns a labeled oligopeptide, obtained by synthesis on a solid phase, by introduction of an appropriate chelating agent according to this invention into the oligopeptide structure on an oligopeptide synthesizer, followed by deprotection and optionally also introduction of a metal ion.

According to a seventh aspect, this invention concerns a labeled oligonucleotide, obtained by synthesis on a solid phase, by introduction of an appropriate chelating agent according to this invention into the oligonucleotide structure on an oligonucleotide synthesizer, followed by deprotection and optionally also introduction of a metal ion.

According to an eighth aspect, this invention concerns a solid support conjugated with the chelating agent according to claim 1, suitable for use in the synthesis of an oligonucleotide, wherein the reactive group A is connected to the chelating agent via a linker x, and A is -E-O-x'- where x' is a linker connected to a solid support, and is the same or different as the linker x E is absent or is a radical of a purine or pyrimidine or any other modified base suitable for use in the synthesis of modified oligonucleotides, said base being connected to the oxygen atom via either
i) a hydrocarbon chain, which is substituted with a protected hydroxyethyl group, or via
ii) a furan ring or pyrane ring or any modified furan or pyrane ring, suitable for use in the synthesis of modified oligonucleotides.

DETAILED DESCRIPTION OF THE INVENTION

Chelating Agents

Chelating agents and metal chelates based thereon where the chromophoric moiety, which most commonly is a bivalent aromatic structure comprising one or more trialkoxyphenyl pyridyl groups, are new. The trialkoxyphenyl pyridyl group is capable of absorbing light or energy and transferring the excitation energy to the chelated lanthanide ion, giving rise to a strong fluorescense irrespective of the lanthanide ion used. In addition to the trialkoxyphenyl pyridyl group or groups, the chromophoric unit may comprise unsubstituted pyridyl groups, pyridyl groups bearing other substituents and/or other aromatic groups.

In the compounds demonstrated by specific examples herein, the 4-position of the pyridyl group bears the trialkoxyphenyl substituent. Although this position is believed to be the most preferable, other positions of the pyridine ring may also be useful for substitution.

Preferably, the alkoxy groups are $C_1$-$C_4$ alkoxy groups.

According to a preferable embodiment, the chromophoric moiety comprises two or three pyridyl groups, wherein at least one of them is substituted with a trialkoxyphenyl group. These pyridyl groups can be tethered directly to each other to form a bipyridyl or terpyridyl group, respectively. Alternatively, and more preferably, the pyridyl groups are tethered to each other via N-containing hydrocarbon chains. The N-containing hydrocarbon chain shall be understood as a chain containing no other heteroatoms than N or no aromatic groups. In this case chelates with very good stability can be obtained. Chelating agents of this structure give metal chelates stable enough also for in vivo use in MRI and/or PET applications.

In case the chelating part is attached to the aromatic unit of the chromophoric moiety, it can be attached to the pyridine ring or to a substituent thereon such as the phenyl group.

The chelating agent or chelate must bear a reactive group A in order to enable covalent binding of the chelating agent or chelate to a biomolecule or to a solid support. However, there exist applications where no such covalent binding is necessary. Chelating compounds of this invention can also be used in applications where no reactive group in the chelate is needed. One example of this kind of technology is demonstrated e.g. in Blomberg, et al., *J. Immunological Methods*, 1996, 193, 199. Another example where no reactive group A is needed is the separation of eosinophilic and basophilic cells. In this application positively and negatively charged chelates bind negatively and positively charged cell surfaces, respectively.

Although that a reactive group A in principle in many applications could be attached directly to the chromophoric group or to the chelating part, it is highly desirable, especially for steric reasons, to have a linker x between the reactive group A and the chromophoric group or chelating part, respectively. The linker is especially important in case the chelate shall be used in solid phase syntheses of oligopeptides and oligonucleotides, but it is desirable also in labeling biomolecules in solution.

According to a preferable embodiment, the reactive group A is selected from the group consisting of isothiocyanate, haloacetamido, maleimido, dichlorotriazinyl, dichlorotriazinylamino, pyridyldithio, thioester, aminooxy, hydrazide, amino, a polymerizing group, and a carboxylic acid or acid halide or an active ester thereof. Particularly in case the chelate or chelating agent shall be attached to microparticle or nanoparticle it is preferable to have a reactive group which is a polymerizing group. In this case the label can be introduced in the particle during the manufacturing of the particles.

The linker x is preferably formed from one to ten moieties, each moiety being selected from the group consisting of phenylene, alkylene containing 1-12 carbon atoms, ethynydiyl (—C≡C—), ethylenediyl (—C═C—), ether (—O—), thioether (—S—), amide (—CO—NH—, —CO—NR'—, NH—CO— and —NR'—CO—), carbonyl (—CO—), ester (—COO— and —OOC—), disulfide (—SS—), diaza (—N=N—), and tertiary amine, wherein R' represents an alkyl group containing less than 5 carbon atoms.
According to a particularly preferable embodiment, the chelating agent is one of the following specific structures:
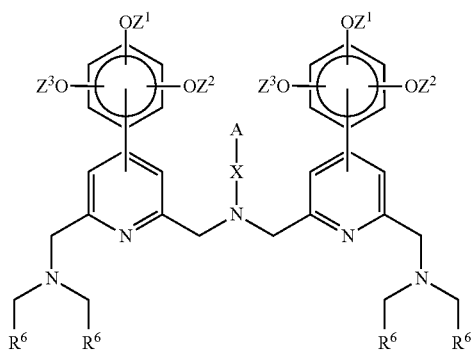
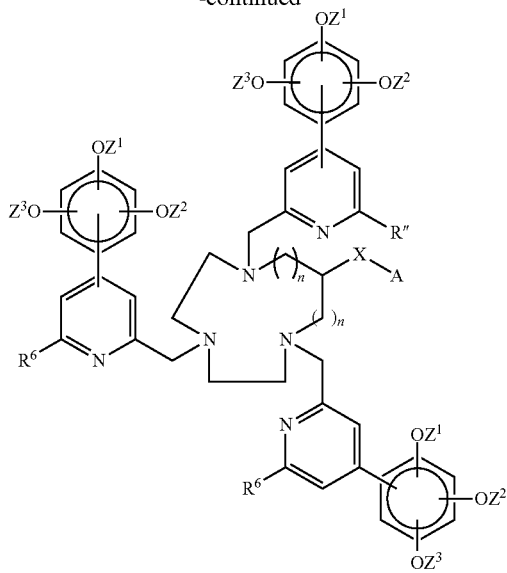
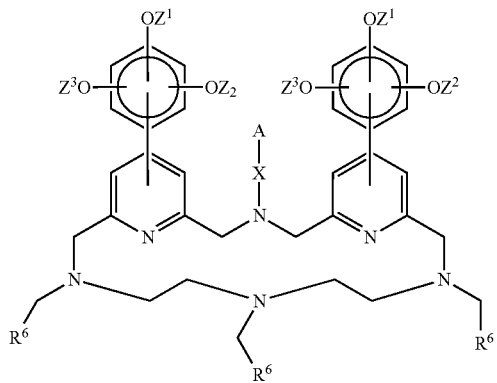
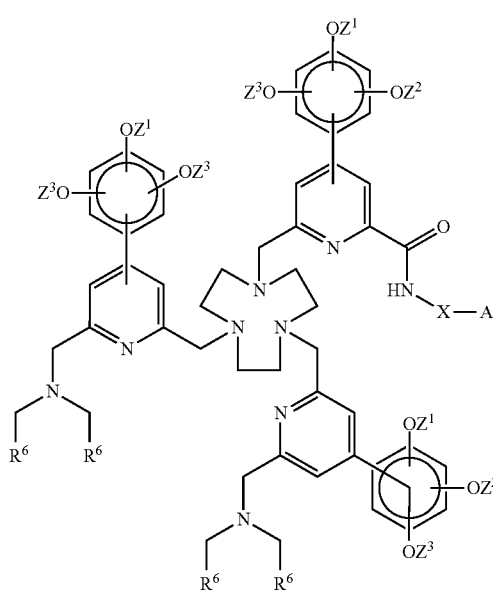

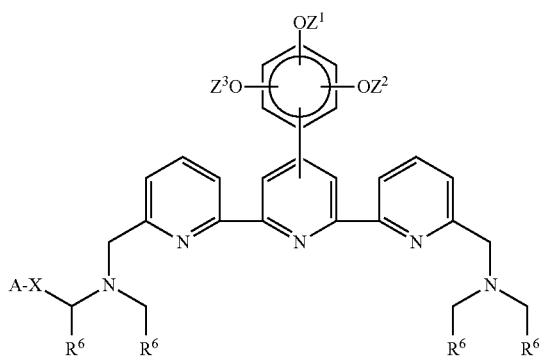

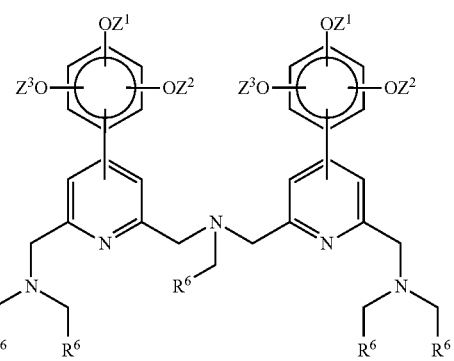

where $Z^1$, $Z^2$ and $Z^3$ are same or different alkyl groups; $R^6$ is an alkyl ester or allyl ester; $R^7$ is an alkyl group and n is 0 or 1.

Chelating Agents for Use in Peptide Synthesis

According to one preferred embodiment, the chelating agent according to this invention is suitable for use in the synthesis of an oligopeptide. In this application, the reactive group A is connected to the chelating agent via a linker x, and A is an amino acid residue —CH(NHR$^1$)R$^5$ where R$^1$ is a transient protecting group and R$^5$ is a carboxylic acid or its salt, acid halide or an ester. Particularly preferable chelating agents are the structures

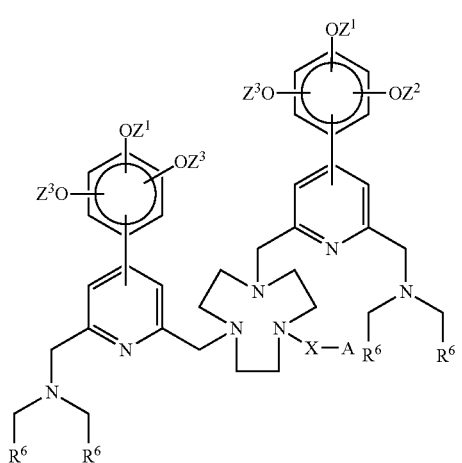

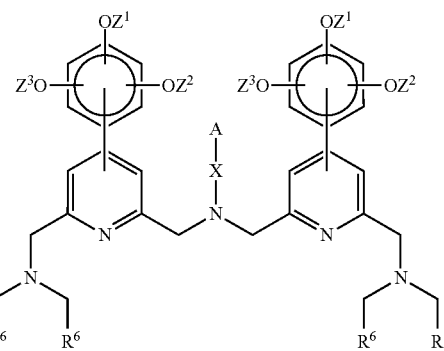

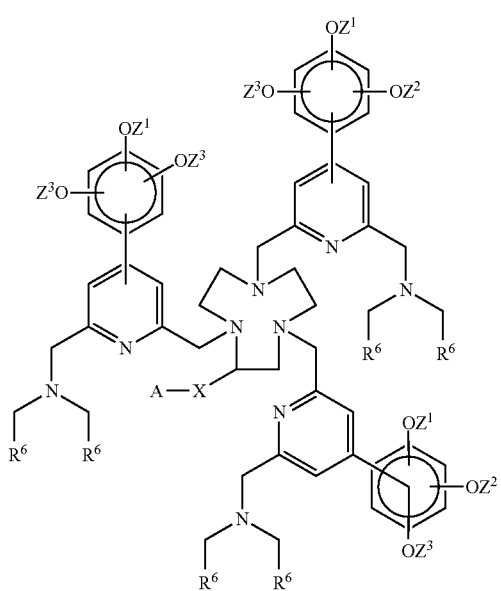

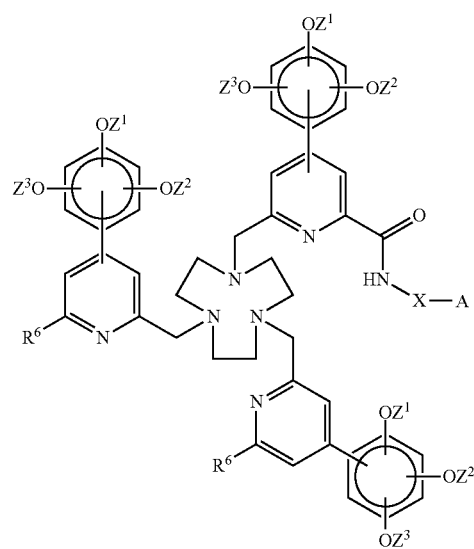

9
-continued
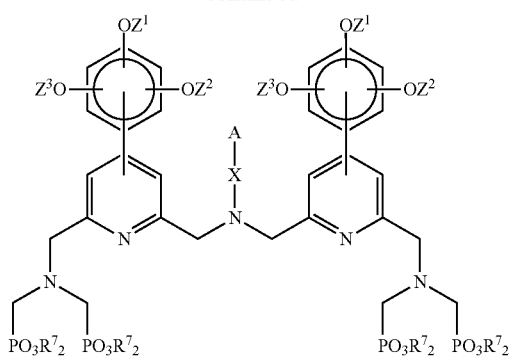
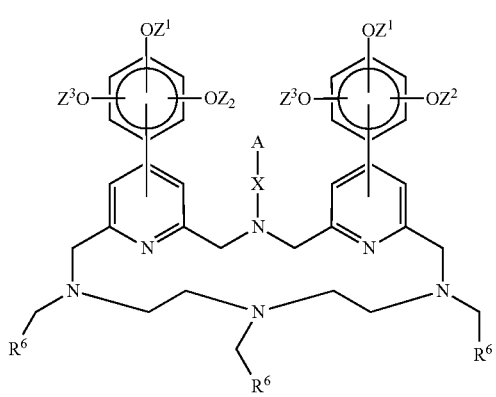
10
-continued
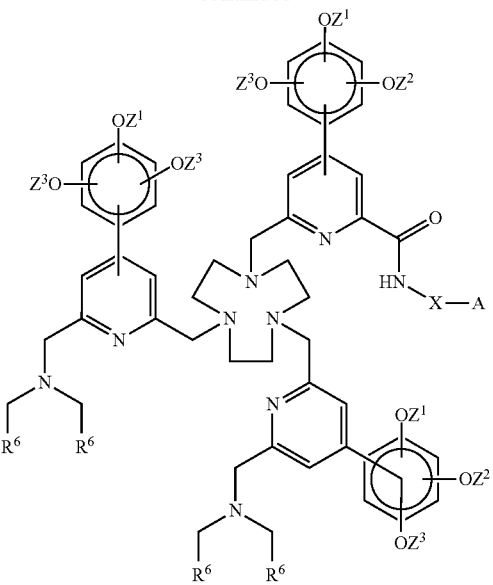
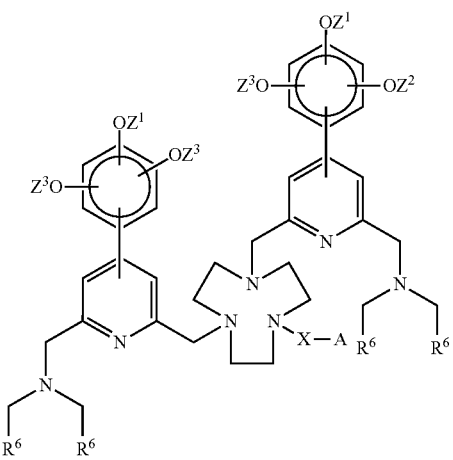

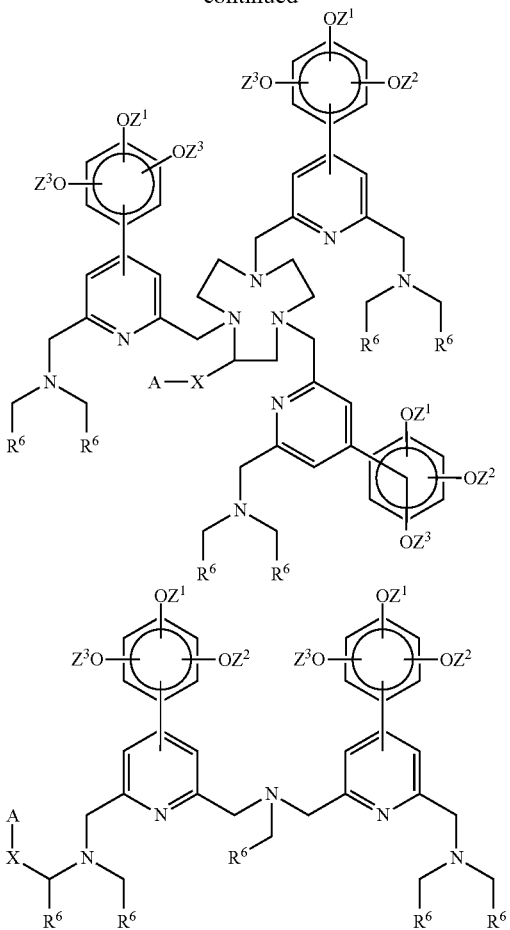

wherein x is as defined before and the protecting group $R^1$ is selected from a group consisting of Fmoc (fluorenylmethoxycarbonyl), Boc (tert-butyloxycarbonyl), or Bsmoc (1,1-dioxobenzo[b]thiophen-2-ylmethyloxycarbonyl), and $R^6$ is an alkyl ester or an allyl ester and $R^7$ is an alkyl group, and $Z^1$, $Z^2$ and $Z^3$ are alkyl groups, same or different, and n is 0 or 1.

The chelating agent can be introduced into biomolecules with the aid of peptide synthesizer. The chelating agent can be coupled to an amino tethered solid support or immobilized amino acid e.g. by carbodiimide chemistry (i.e. the carboxylic acid function of the labeling reagent reacts with the amino group of the solid support or amino acid in the presence of an activator). When the condensation step is completed the transient amino protecting group of the labeling reagent is selectively removed while the material is still attached to the solid support (e.g with piperidine in the case of Fmoc-protecting group). Then second coupling of a chelating agent or other reagent (amino acid, hapten) is performed as above. When the synthesis of the desired molecule is completed, the material is detached from the solid support and deprotected. Purification can be performed by HPLC techniques. Finally the purified ligand is converted to the corresponding lanthanide(III) chelate by addition of known amount of lanthanide(III) ion.

Chelating Agents for Use in Oligonucleotide Synthesis

According to another preferred embodiment, the chelating agent according to this invention is suitable for use in the synthesis of an oligonucleotide. In this case the reactive group A is connected to the chelating agent via a linker x, and A is

-E-O—PZ—O—$R^4$ where one of the oxygen atoms optionally is replaced by sulfur, Z is chloro or $NR^2R^3$, $R^4$ is a protecting group, $R^2$ and $R^3$ are alkyl groups, and E is absent or is a radical of a purine base or a pyrimidine base or any other modified base suitable for use in the synthesis of modified oligonucleotides. Said base is connected to the oxygen atom either via i) a hydrocarbon chain, which is substituted with a protected hydroxyethyl group, or via ii) a furan ring or pyrane ring or any modified furan or pyrane ring, suitable for use in the synthesis of modified oligonucleotides.

The chelating agent can be introduced into oligonucleotides with the aid of oligonucleotide synthesizer. A useful method, based on a Mitsonobu alkylation (J Org Chem, 1999, 64, 5083; Nucleosides, Nucleotides, 1999, 18, 1339) is disclosed in EP-A-1152010. Said patent publication discloses a method for direct attachment of a desired number of conjugate groups to the oligonucleotide structure during chain assembly. Thus solution phase labeling and laborious purification procedures are avoided. The key reaction in the synthesis strategy towards nucleosidic oligonucleotide building blocks is the aforementioned Mitsunobu alkylation which allows introduction of various chelating agents to the nucleoside, and finally to the oligonucleotide structure. The chelating agents are introduced during the chain assembly. Conversion to the lanthanide chelate takes place after the synthesis during the deprotection steps.

Normal, unmodified oligonucleotides have low stability under physiological conditions because of its degradation by enzymes present in the living cell. It may therefore be desirable to create a modified oligonucleotide according to known methods so as to enhance its stability against chemical and enzymatic degradation. Modifications of oligonucleotides are extensively disclosed in prior art. Reference is made to U.S. Pat. No. 5,612,215. It is known that removal or replacement of the 2'-OH group from the ribose unit in an RNA chain gives a better stability. WO 92/07065 and U.S. Pat. No. 5,672,695 discloses the replacement of the ribose 2'-OH group with halo, amino, azido or sulfhydryl groups. U.S. Pat. No. 5,334,711 disclose the replacement of hydrogen in the 2'-OH group by alkyl or alkenyl, preferably methyl or allyl groups. Furthermore, the internucleotidic phosphodiester linkage can, for example, be modified so that one or more oxygen is replaced by sulfur, amino, alkyl or alkoxy groups. Preferable modifications in the internucleotide linkages are phosphorothioate linkages. Also the base in the nucleotides can be modified.

Preferably E is a radical of any of the bases thymine, uracil, adenosine, guanine or cytosine, and said base is connected to the oxygen atom via i) a hydrocarbon chain, which is substituted with a protected hydroxyethyl group, or via ii) a furan ring having a protected hydroxyethyl group in its 4-position and optionally a hydroxyl, protected hydroxyl or modified hydroxyl group in its 2-position.

Preferably a reactive group -E-O—P($NR^2R^3$)—O—$R^4$ has a structure selected from one of the following structures:

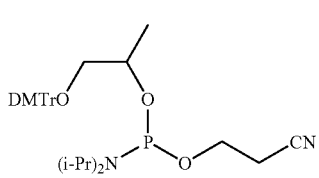

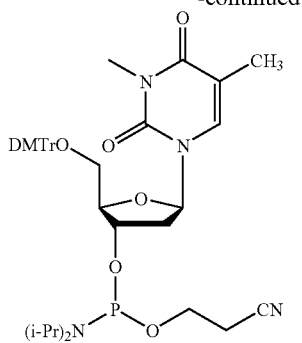
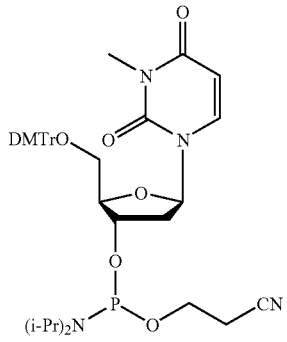
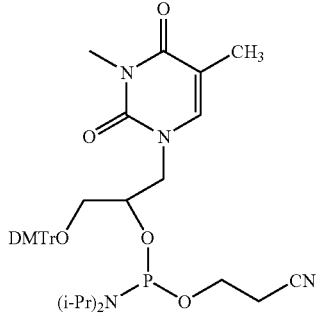
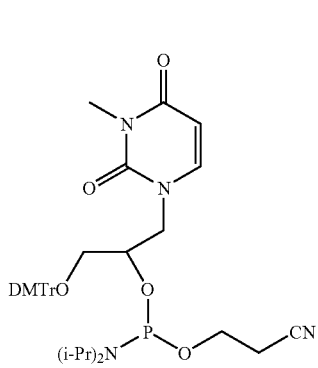
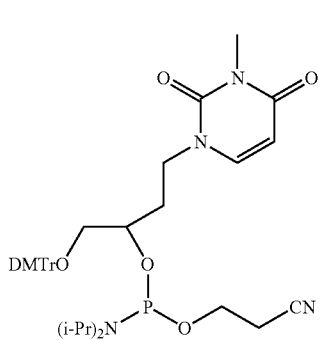
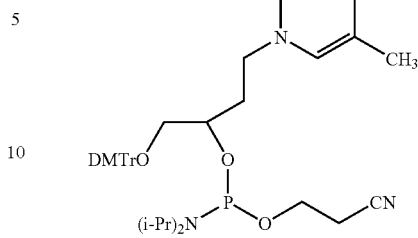
where —is the position of the linker x and DMTr is dimethoxytrityl.
A particularly preferable chelating agent is selected from one of the specific structures disclosed below
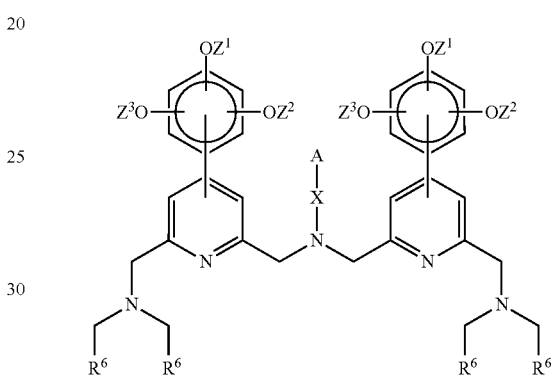
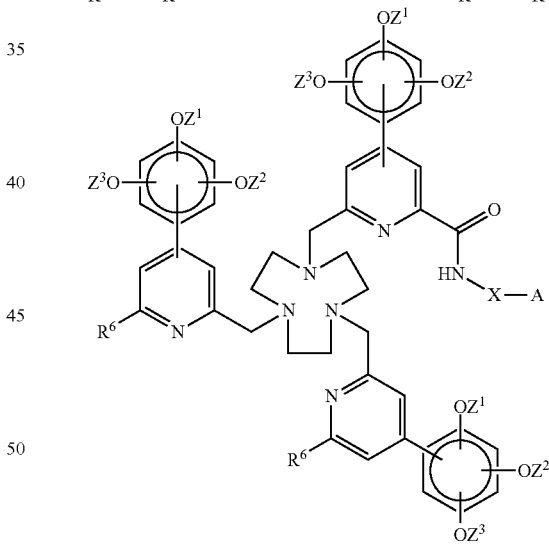

15
-continued
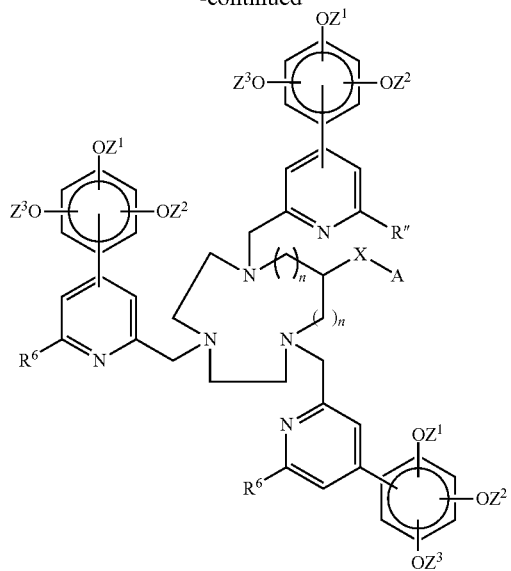
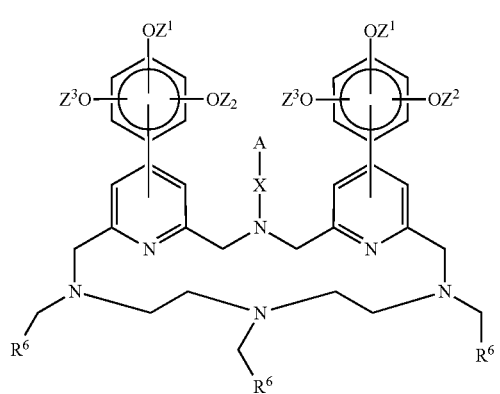
16
-continued
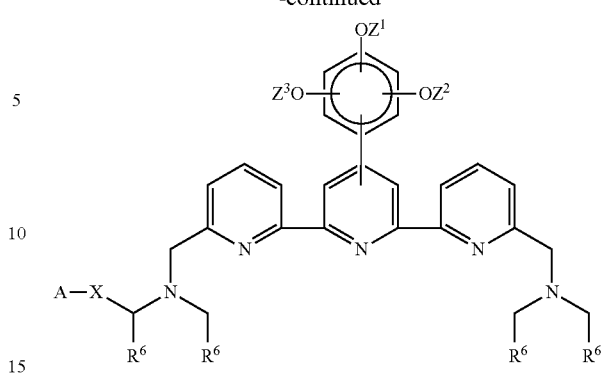
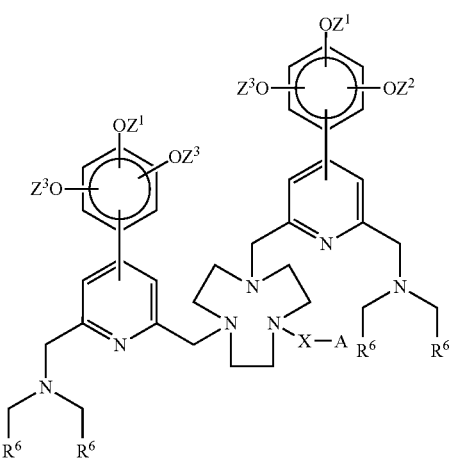
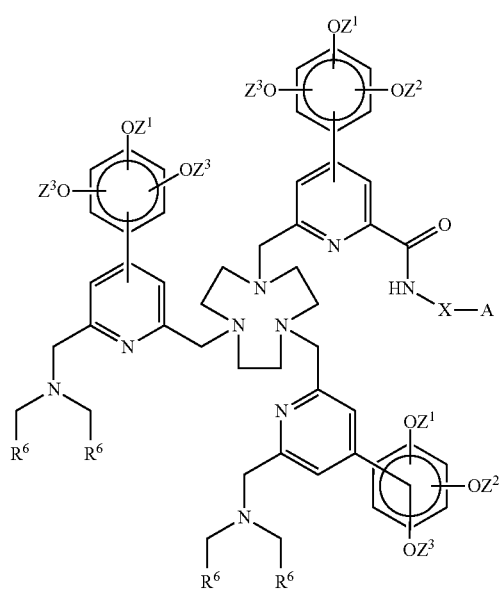
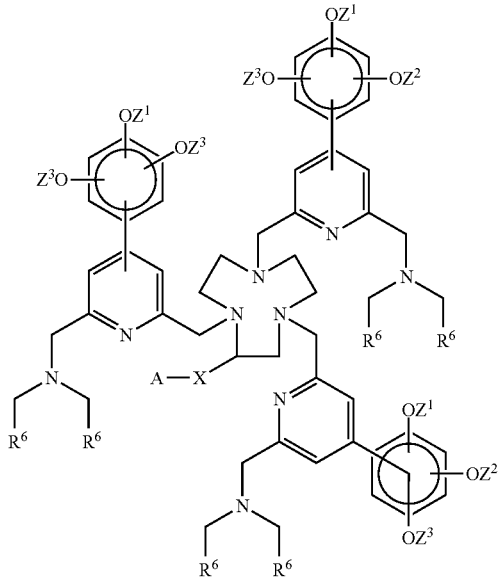

17
-continued

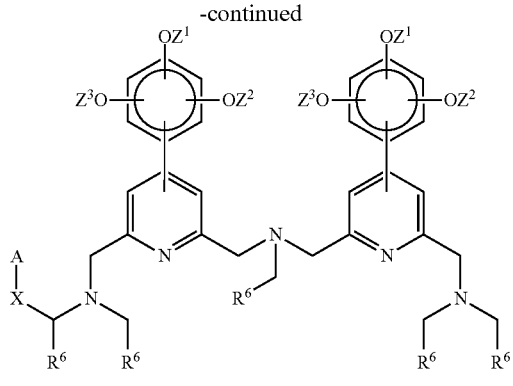

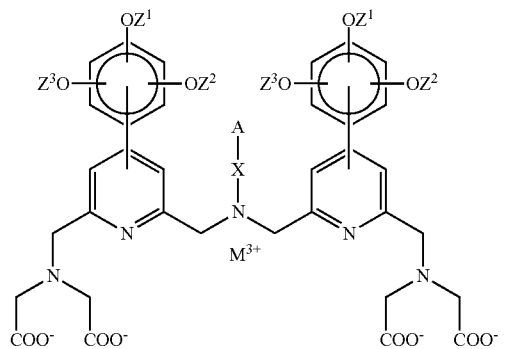

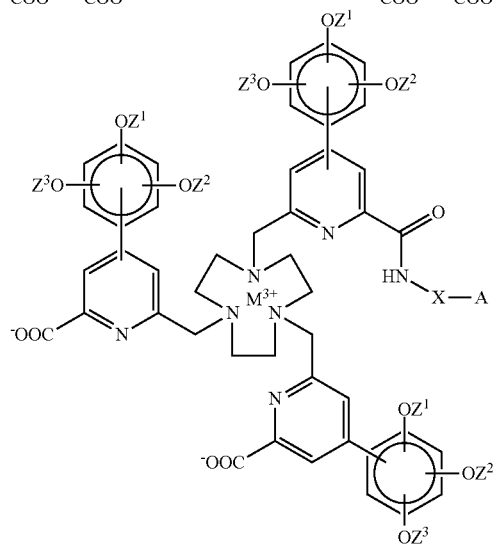

18
-continued

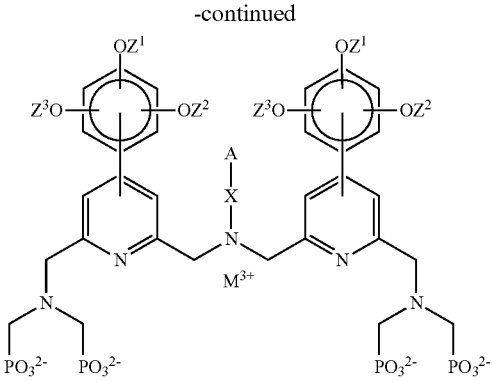

where $R^6$ is an alkyl ester or an allyl ester and $R^7$ is an alkyl group and wherein x is as defined before and A is -E-O—P($NR^2R^3$)—O—$R^4$ as defined above and $Z^1$, $Z^2$ and $Z^3$ are the same or different alkyl groups, and n is 0 or 1.

Chelates

The chelates comprise a chelating agent as described above and a chelated metal ion.

In case the chelate is to be used in bioaffinity assays, the chelated metal ion is preferably a lanthanide, especially europium(III), samarium(III), terbium(III) or dysprosium (III). The chelating agent is preferably one of the preferable agents mentioned above.

Particularly preferable lanthanide chelates are

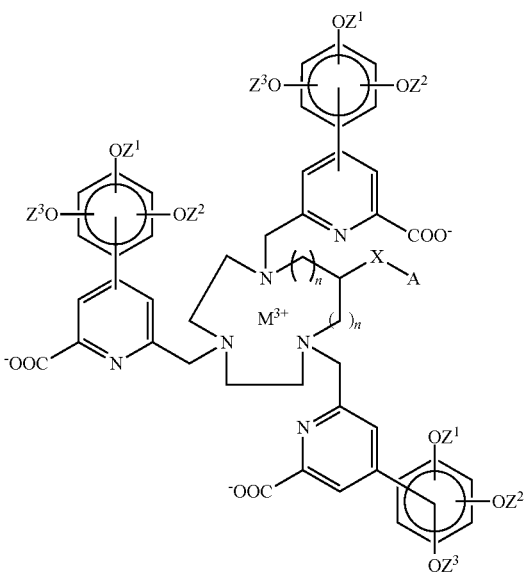

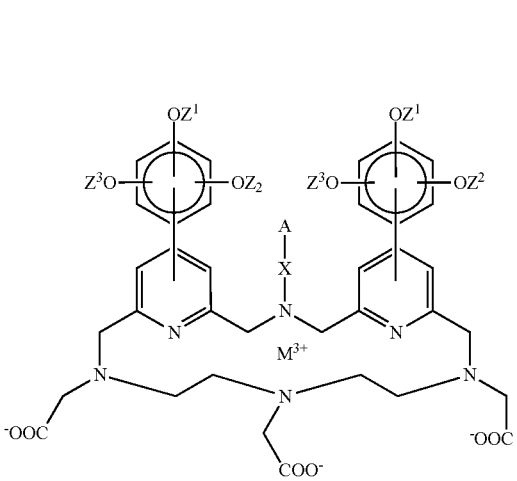

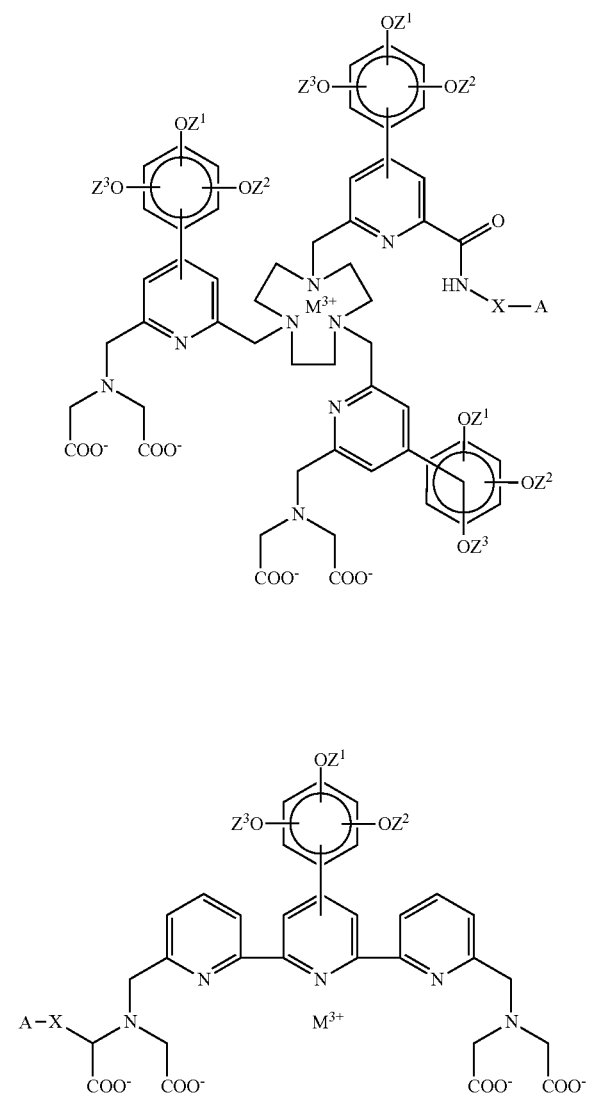
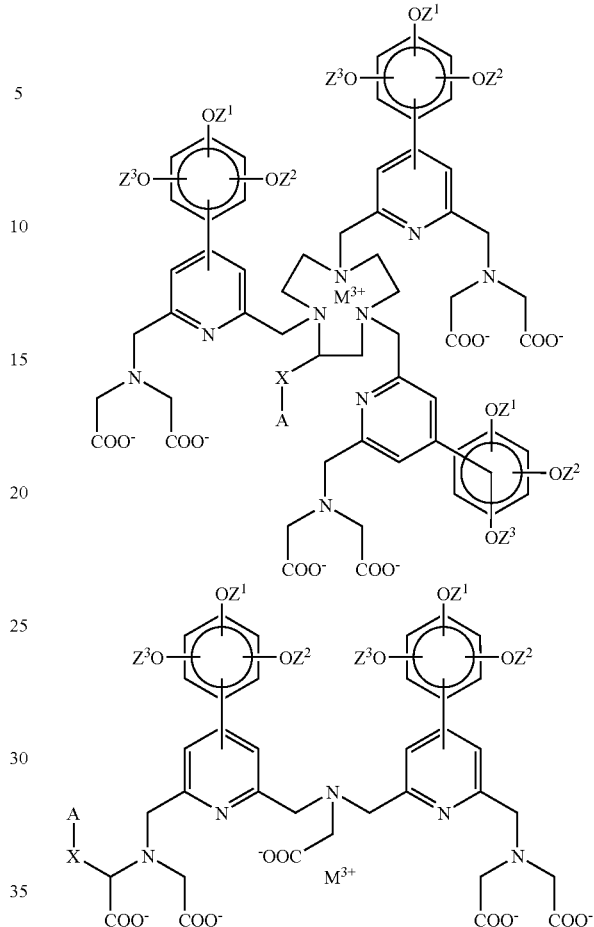

where $Z^1$, $Z^2$ and $Z^3$ are the same or different alkyl groups, and n is 0 or 1.

The chelates according to this invention can also be used in vivo in MRI applications or in PET applications. A preferable metal to be used in MRI is gadolinium. In PET applications a radioactive metal isotope is introduced into the chelating agent just before use. Particularly suitable radioactive isotopes are Ga-66, Ga-67, Ga-68, Cr-51, In-111, Y-90, Ho-166, Sm-153, Lu-177, Er-169, Tb-161, Dy-165, Ho-166, Ce-134, Nd-140, Eu-157, Er-165, Ho-161, Eu-147, Tm-167 and Co-57. In order to obtain very stable chelates, it is preferable to have a chromophoric moiety where there are several pyridyl groups tethered to each other via N-containing hydrocarbon chains.

Biomolecules

The biomolecule conjugated with a chelating agent or a chelate according to this invention is preferably an oligopeptide, oligonucleotide, DNA, RNA, modified oligo- or polynucleotide, such as phosphoromonothioate, phosphorodithioate, phosphoroamidate and/or sugar- or basemodified oligo- or polynucleotide, protein, oligosaccharide, polysaccaride, phospholipide, PNA, LNA, antibody, hapten, drug, receptor binding ligand and lectine.

Solid Support Conjugates

The chelates, chelating agents and biomolecules according to this invention may be conjugated on a solid support. The solid support is preferably a particle such as a microparticle or nanoparticle, a slide or a plate.

In case the chelate or chelating agent has a polymerizing group as reactive group, then the chelate or chelating agent

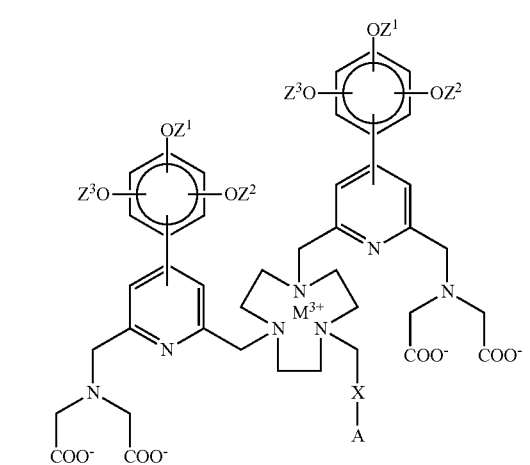

may be introduced in the solid support, for example a particle, simultaneously with the preparation of the particles.

The biomolecule conjugated with the solid support, either covalently or noncovalently is preferable a labeled oligopeptide, obtained by synthesis on a solid phase, by introduction of a chelating agent into the oligopeptide structure on an oligopeptide synthesizer, followed by deprotection and optionally introduction of a metal ion. Alternatively, the biomolecule conjugated with the solid support, either covalently or noncovalently is preferable a labeled oligonucleotide, obtained by synthesis on a solid phase, by introduction of a chelating agent into the oligonucleotide structure on an oligonucleotide synthesizer, followed by deprotection and optionally introduction of a metal ion.

A solid support conjugated with a chelating agent having a reactive group A which is connected to the chelating agent via a linker x, and A is -E-O-x'- as defined before, is suitable for use in oligonucleotide syntheses.

The invention will be illuminated by the following non-restrictive Examples.

EXAMPLES

The invention is further elucidated by the following examples. The structures and synthetic routes employed in the experimental part are depicted in Schemes 1-7. Scheme 1 illustrates the synthesis of the oligopeptide labeling reactant 4. The experimental details are given in Examples 1-4. Scheme 2 illustrates the synthesis of the chelates 6-11. Experimental details are given in Examples 6-11. Scheme 3 illustrates the synthesis of the chelates 20, 22 and 23. Experimental details are given in Examples 12-23. Scheme 4 illustrates the synthesis of the building block 29 designed for the introduction of lanthanide chelates to the oligonucletides on solid phase as well as synthesis of the chelates 30 and 31. Experimental details are given in Examples 24-31. Schemes 5 and 6 illustrate the use of building blocks 4 and 29 in the preparation of synthetic oligopeptides and oligonucletides, respectively on solid phase. Experimental details are given in Examples 32 and 33. Scheme 7 illustrates the preparation of oligonucleotide labeling reagents based on 1,4,7-triazecane. Experimental details are given in Example 34.

Photochemical properties of illustrative examples of the chelates synthesized are collected in Table 1.

Experimental Procedures

Reagents for machine assisted oligopeptide synthesis were purchased from Applied Biosystems (Foster City, Calif.). Adsorption column chromatography was performed on columns packed with silica gel 60 (Merck). NMR spectra were recorded either on a Brucker 250 or a Jeol LA-400 spectrometers operating at 250.13 and 399.8 MHz for $^1$H, respectively. Me$_4$Si was used as an internal reference. Coupling constants are given in Hz. IR spectra were recorded on a Perkin Elmer 2000 FT-IR spectrophotometer. Electrospray mass spectra were recorded on an Applied Biosystems Mariner ESI-TOF instrument. Oligopeptides were assembled on an Applied Biosystems 433A Synthesizer and oligonucleotides on an Applied Biosystems Expedite instrument using recommended protocols. Fluorescence spectra were recorded on a PerkinElmer LS 55 instrument.

The syntheses of the compounds are carried out as outlined in Schemes 1 to 7 below.

Example 1

The synthesis of tetra(tertbutyl) 2,2',2'',2'''-{[6-N-(4-methoxytrityl)aminohexyl-imino]bis(methylene)bis[4-(2,4,6-trimethoxyphenyl)pyridine-6,2-diyl]bis(methylenenitrilo)}tetrakis(acetate) 1

Tetra(tert-butyl) 2,2',2'',2'''-{[6-N-(4-methoxytrityl)hexylimino]bis(methylene)bis-(4-bromopyridine-6,2-diyl)bis(methylenenitrilo)}tetrakis(acetate) (4.0 g, 2.4 mmol) and trimethoxyphenylboronic acid (1.1 g, 5.3 mmol) were dissolved in dry DMF (50 mL) and Cs$_2$CO$_3$ (2.0 g, 6.0 mmol) and Pd(PPh$_3$)$_4$ (0.1 g, 96 μmol) were added. After stirring overnight at 950, trimethoxyphenylboronic acid (0.5 g, 2.4 mmol), Cs$_2$CO$_3$ (0.79 g, 2 mmol) and Pd(PPh$_3$)$_4$ (50 mg, 43 mmol) were added. After overnight reaction the mixture was cooled to room temperature, filtered and evaporated. The mixture was dissolved in CH$_2$Cl$_2$ and washed with water (2·40 ml). The product was purified by flash chromatography (silica gel, petroleum ether (40-60°)/AcOEt/TEA 5:2:1, v/v/v). Yield was 3.1 g (90%). IR (film): 1737 (C=O), 1128 (C—O). $^1$H NMR (CDCl$_3$): δ 1.15-1.25 (4H, m); 1.40-1.45 (40H, m); 2.04 (2H, t, J 6); 2.55 (2H, t, J 7); 3.50 (1H, s); 3.51 (3H, s). ESI-MS: [M+H]$^+$ 1417.5 calc. for C$_{82}$H$_{109}$N$_6$O$_{15}$$^+$ 1417.8.

Example 2

The synthesis of tetra(tert-butyl) 2,2',2'',2'''-{(6-aminohexylimino)bis(methylene)-bis[4-(2,4,6-trimethoxyphenyl)pyridine-6,2-diyl]bis(methylenenitrilo)}tetrakis-(acetate) 2

Compound 1 (1.0 g, 0.7 mmol) was dissolved in dichloromethane (25 mL) and trifluoroacetic acid (0.25 mL) was added. After stirring for 4 hours at ambient temperature the mixture was washed with sat. NaHCO$_3$ (2·50 mL). The organic phase was dried over Na$_2$SO$_4$, filtered and evaporated. The product was purified by flash chromatography (silica gel, petroleum ether (40-60°)/AcOEt/TEA 5:5:1, 2:5:1 and finally 10% MeOH, 1% TEA in CH$_2$Cl$_2$). Yield was 0.60 g (74%). IR (film): 1730 (C=O), 1128 (C—O). ESI-MS: [M+H]$^+$ 1145.7 calc. for C$_{82}$H$_{109}$N$_6$O$_{15}$$^+$ 1145.7; [M+2H]$^{2+}$ 573.3, calc. 573.3.

Example 3

The Synthesis of the Allyl Protected Oligopeptide Labeling Reactant 3

Compound 2 (0.55 g, 0.48 mmol) was dissolved in dry dichloromethane (5 mL). DCC (0.11 g, 0.53 mmol) and Fmoc-Glu-OAll (0.20 g, 0.48 mmol) were added, and the mixture was stirred overnight at room temperature. DCU formed was filtered off and the filtrate was concentrated in vacuo. Purification on silica gel (10% MeOH in dichloromethane) yielded the title compound as a solid (300 mg). ESI-MS: [M+H]$^+$ 1536.8 calc. for C$_{85}$H$_{114}$N$_7$O$_{19}$$^+$ 1536.8.

Example 4

The Synthesis of the Oligopeptide Labeling Reactant 4

Compound 3 (157 mg, 0.1 mmol) was dissolved in dry dichloromethane (2 mL). Pd(Ph$_3$P)$_4$ (2.3 mg) and PhSiH$_3$ (25 μL) were added, and the mixture was stirred overnight at ambient temperature. The reaction mixture was then washed with 10% aq. citric acid and dried over molecular sieves. Yield was 95 mg (63%). ESI-MS: [M+H]$^+$ 1496.8 calc. for $C_{82}H_{110}N_7O_{19}{}^+$ 1496.8.

Example 5

The Synthesis of Free Acid 5

Compound 1 (0.40 g, 0.28 mmol) was dissolved in trifluoroacetic acid (10 mL), stirred for 1 h at room temperature and concentrated. The residue was triturated with diethyl ether. The product was collected by filtration and dried. Yield was 260 mg (100%). ESI-MS: [M+H]$^+$ 921.42 calc. for $C_{46}H_{61}N_6O_{14}{}^+$ 921.4.

Example 6

The Synthesis of the Terbium Chelate 6

Compound 5 (78 mg, 0.085 mmol) was dissolved in water (2 mL) and terbium(III) chloride (35 mg, 0.093 mmol) was added during 15 min at pH 6.5. After 2 h at room temperature pH of the reaction mixture was increased to 8.5 by addition of 1 M NaOH. The precipitation formed was removed by centrifugation, the aqueous phase was concentrated and the product was precipitated with acetone. ESI-MS: [M+H]$^+$ 1075.9 calc. for $C_{46}H_{55}N_6O_{14}Tb^-$ 1075.3.

Example 7

The Synthesis of the Dysprosium Chelate 7

Synthesis was performed as in Example 6 but using dysprosium (III) chloride. ESI-MS: [M+H]$^+$ 1080.3 calc. for $C_{46}H_{55}N_6O_{14}Dy^-$ 1080.2.

Example 8

The Synthesis of the Europium Chelate 8

Synthesis was performed as in Example 6 but using europium(III) chloride. ESI-MS: [M+H]$^+$ 1092.3 calc. for $C_{46}H_{55}N_6O_{14}Eu^-$ 1092.3.

Example 9

The Synthesis of the Iodoacetamido Activated Dysprosium Chelate 9

Compound 7 (16 mg, 14.3 μmol) was dissolved in water. Iodoacetic anhydride (51.3 mg, 0.145 mmol; predissolved in 0.2 mL of chloroform) and DIPEA (25 μL) were added and the mixture was stirred for 1.5 h at room temperature. The organic phase was removed, and the product was isolated from the aqueous phase by precipitation from THF. ESI-MS: [M+H]$^+$ 1248.2 calc. for $C_{48}H_{57}N_6O_{15}IDy^-$ 1248.2.

Example 10

The Synthesis of the Iodoacetamido Activated Terbium Chelate 10

Activation of compound 6 as described in Example 9 yielded compound 10. ESI-MS: [M+H]$^+$ 1243.8 calc. for $C_{48}H_{57}N_6O_{15}ITb^-$ 1243.8.

Example 11

The Synthesis of the Isothiocyatano Activated Europium Chelate 11

Compound 8 (15 mg, 0.014 mmol) was dissolved in the mixture of pyridine, water and triethylamine (200 μL; 9:1.5:0.1; v/v/v). 1,4-phenylenediisothiocyanate (7.9 mg) was added and the mixture was stirred for 4 h at room temperature.

Example 12

The synthesis of diethyl 4-(2,4,6-trimethoxyphenyl) pyridine-2,6-dicarboxylate 12

2,4,6-trimethoxyphenylboronic acid (2.12 g, 10.0 mmol) and diethyl 4-bromopyridine-2,6-dicarboxylate (3.33 g, 11.0 mmol) were dissolved in dry DMF (50 mL). Caesium carbonate (4.56 g, 14.0 mmol) and tetrakis(triphenylphosphine)-palladium(0) (0.23 g, 0.20 mmol) were added, and the mixture was deaerated with argon. The mixture was heated at 95° C. for 48 h. The mixture was allowed to cool to room temperature and filtered. The filtrate was concentrated in vacuo, the residue was dissolved in chloroform (60 mL) and washed with 10% aq. citric acid and water, dried over $Na_2SO_4$ and concentrated. Purification was performed on silica gel (eluent petroleum ether bp 40-60° C.; ethyl acetate 5:3→2:5, v/v). Yield was 2.09 g (54%). $^1$H NMR (CDCl$_3$): δ 1.45 (6H, t, J 7.1); 3.74 (6H, s); 3.90 (3H, s); 4.49 (4H, q, J 7.1); 6.22 (2H, s); 8.28 (2H, s). IR (film)/cm$^{-1}$ 1743, 1610 (C═O); 1339, 1238, 1128 (C—O). ESI-MS: [M+H]$^+$ 390.19 calc. for $C_{20}H_{24}NO_7{}^+$ 390.15.

Example 13

The synthesis of 4-(2,4,6-trimethoxyphenyl)-6-(hydroxymethyl)pyridine-2-carboxylic acid ethyl ester 13

Compound 12 (2.83 g, 7.27 mmol) was suspended in ethanol (140 mL), and the mixture was heated to 45° C. Sodium borohydride (0.29 g) was added, and the mixture was stirred for 1 h and allowed to cool to room temperature. pH of the solution was adjusted to 3 with 6 M HCl and concentrated. The residue was suspended in dichloromethane and washed with sat. NaHCO$_3$. The organic layer was dried over $Na_2SO_4$ and purified on silica gel (eluent petroleum ether bp 40-60° C.:ethyl acetate:triethylamine, 2:5:1; v/v/v). ESI-MS: [M+H]$^+$ 348.14 calc. for $C_{18}H_{22}NO_6{}^+$ 348.14.

Example 14

The synthesis of 4-(2,4,6-trimethoxyphenyl)-6-(bromomethyl)pyridine-2-carboxylic acid ethyl ester 14

Phosphorus trichloride (0.778 g, 2.87 mmol) was dissolved in dry DMF (10 mL) at 0° C. Compound 13 (1.0 g, 2.8 mmol) was added, and the mixture was stirred at room temperature for 3.5 h before being neutralized with sat. NaHCO$_3$. The mixture was extracted with dichloromethane. The organic phase was dried, concentrated and purified on silica gel using (eluent 1% ethanol in dichloromethane). ESI-MS: [M+H]$^+$ 410.10 calc. for $C_{18}H_{21}BrNO_5{}^+$ 410.05.

Example 15

The synthesis of N-(2-(2,2,2-trifluoroacetamido) ethyl)-6-(hydroxymethyl)-4-(2,4,6-trimethoxyphenyl)pyridine-2-carboxamide 15

Compound 13 (1.0 g, 2.8 mmol) was dissolved in ethylenediamine (10 mL), stirred for 2.5 h at room temperature and concentrated (oil pump). The residue was dissolved in DMF (25 mL) and ethyl trifluoroacetate (5 mL) was added. After 2 h at room temperature all volatiles were removed in vacuo, and the residue was purified on silica gel (eluent 10% MeOH in dichloromethane. ESI-MS: $[M+H]^+$ 458.14 calc. for $C_{20}H_{23}F_3N_3O_6^+$ 458.15.

Example 16

The synthesis of N-(2-(2,2,2-trifluoroacetamido) ethyl)-6-(bromomethyl)-4-(2,4,6-trimethoxyphenyl) pyridine-2-carboxamide 16

Bromination of compound 15 as described in Example 14 yielded the title compound. ESI-MS: $[M+H]^+$ 520.06 calc. for $C_{20}H_{22}BrF_3N_3O_5^+$ 520.07

Example 17

The synthesis of di-tert-butyl 7-((6-(2-(2,2,2-trifluoroacetamido)ethylcarbamoyl)-4-(2,4,6-trimethoxyphenyl)pyridin-2-yl)methyl)-1,4,7-triazonane-1,4-dicarboxylate 17

[1,4,7]triazacyclononane-1,4-dicarboxylic acid di-tert-butyl ester (0.75 g; 2.3 mmol) and Compound 16 (2.3 mmol) were dissolved in dry DMF (60 mL). 2.0 ml of DIPEA (11.4 mmol) was added and the mixture was stirred overnight at room temperature. Solvent was evaporated to dryness and product was purified on silica gel (eluent: diethyl ether). Yield was 1.20 g. ESI-MS: $[M+H]^+$ 769.34 calc. for $C_{36}H_{52}F_3N_6O_9^+$ 769.37

Example 18

The synthesis of 6-((1,4,7-triazonan-1-yl)methyl)-N-(2-(2,2,2-trifluoroacetamido)-ethyl)-4-(2,4,6-trimethoxyphenyl)pyridine-2-carboxamide 18

Compound 17 (1.0 g; 1.3 mmol) was dissolved in trifluoroacetic acid (25 mL) and the mixture was stirred at room temperature for 30 min. Solvent was evaporated to dryness. ESI-MS: $[M+H]^+$ 569.28 calc. for $C_{26}H_{36}F_3N_6O_5^+$ 569.27

Example 19

The synthesis of ethyl 6-((4-((6-(2-(2,2,2-trifluoroacetamido)ethylcarbamoyl)-4-(2,4,6-trimethoxyphenyl)pyridin-2-yl)methyl)-7-((6-(ethoxycarbonyl)-4-(2,4,6-trimethoxyphenyl)pyridin-2-yl)methyl)-1,4,7-triazonan-1-yl)methyl)-4-(2,4,6-trimethoxyphenyl)pyridine-2-carboxylate 19

Compounds 18 (0.39 g; 0.7 mmol) and 14 (0.43 g; 1.4 mmol) were dissolved in dry acetonitrile (20 mL). $K_2CO_3$ (0.48 g; 3.5 mmol) was added and the mixture was refluxed for 3 hours. The precipitation was filtered off and the solvent was evaporated. The product was purified on silica gel (10% EtOH/CH$_2$Cl$_2$). ESI-MS: $[M+H]^+$ 1227.4 calc. for $C_{62}H_{74}F_3N_8O_{15}^+$ 1227.5

Example 20

The synthesis of 6-((4-((6-(2-aminoethylcarbamoyl)-4-(2,4,6-trimethoxyphenyl)-pyridin-2-yl)methyl)-7-((6-carboxy-4-(2,4,6-trimethoxyphenyl)pyridin-2-yl) methyl)-1,4,7-triazonan-1-yl)methyl)-4-(2,4,6-trimethoxyphenyl)pyridine-2-carboxylic acid dysprosium (III) 20

Compound 19 was dissolved in methanolic 0.1 M potassium hydroxide and stirred for 4 h at room temperature. All volatiles were removed in vacuo. Treatment of the residue with dysprosium chloride yielded the title compound ESI-MS: $[M+H]^+$ 1239.1 calc. for $C_{56}H_{66}DyN_8O_{14}^+$ 1238.4

Example 21

The synthesis of ethyl 6-((4,7-bis((6-(ethoxycarbonyl)-4-(2,4,6-trimethoxyphenyl)-pyridin-2-yl)methyl)-1,4,7-triazonan-1-yl)methyl)-4-(2,4,6-trimethoxyphenyl)-pyridine-2-carboxylate 21

1,4,7-triazacyclononane (31.5 mg) and compound 14 (0.3 g, 0.76 mmol) were dissolved in dry acetonitrile (20 mL) Potassium carbonate (0.17 g) was added and the mixture was refluxed overnight. The mixture was allowed to cool to room temperature, filtered and concentrated. Purification on silica gel (eluent CH$_2$Cl$_2$:EtOH:HOAc; 80:20:1, v/v/v) yielded the title compound (0.17 g, 62%). ESI-MS: $[M+H]^+$ 1117.5 calc. for $C_{60}H_{73}N_6O_{15}^+$ 1117.5

Example 22

The synthesis of 6-((4,7-bis((6-carboxy-4-(2,4,6-trimethoxyphenyl)pyridin-2-yl)methyl)-1,4,7-triazonan-1-yl) methyl)-4-(2,4,6-trimethoxyphenyl)pyridine-2-carboxylic acid dysprosium(III) 22

Deprotection of compound 21 followed by treatment with dysprosium chloride as described in Example 20 yielded the title compound.

Example 23

The synthesis of 6-((4,7-bis((6-carboxy-4-(2,4,6-trimethoxyphenyl)pyridin-2-yl)methyl)-1,4,7-triazonan-1-yl)methyl)-4-(2,4,6-trimethoxyphenyl)pyridine-2-carboxylic acid terbium(III) 23

Deprotection of compound 21 followed by treatment with terbium chloride as described in Example 20 yielded the title compound.

Example 24

The synthesis of 2-dimethyl-4-bromo-6-bromomethyl-2-pyridylmethylimino-(diacetate) 24

4-bromo-2,6-bis(bromomethyl)pyridine (2.66 g, 7.7 mmol) and iminoacetic acid dimethyl ester (1.24 g, 7.7 mmol) were dissolved in dry acetonitrile (60 mL) at 60° C. Potassium carbonate (5.3 g) was added, and the mixture was stirred for 40 min before being cooled to room temperature, filtered and concetrated. The residue was dissolved in dichlo-

Example 25

The synthesis of 2,2',2",2'''-{[6-hydroxyhexylimino]-bis(methylene)bis(4-bromo)pyridine-6,2-diyl)bis(methylenenitrilo)}tetrakis(acetic acid) tetra(methyl ester) 25

Compound 24 (2.8 g, 6.6 mmol) was dissolved in dry DMF. DIPEA (6.0 mL, 34.0 mmol) and 6-amino-1-hexanol (0.2 g, 3.6 mmol) were added, and the reaction mixture was stirred at 60° C. for 4 hours before being evaporated to dryness. The residue was dissolved in $CH_2Cl_2$ (30 mL) and was washed twice with water. The organic phase was dried over $Na_2SO_4$ and evaporated to dryness. The product was purified by silica gel chromatography (0 to 3% MeOH in $CH_2Cl_2$) to yield 2.4 g (91%) of Compound 25. ESI-MS: $[M+H]^+$ 802.16; calcd. for $C_{32}H_{46}Br_2N_5O_9^+$ 802.22.

Example 26

The synthesis of 2,2',2",2'''-{[6-(-methoxytrityloxy-hexylimino]bis(methylene)bis(4-bromo)pyridine-6,2-diyl)bis(methylenenitrilo)}tetrakis(acetic acid) tetra(methyl ester) 26

Compound 25 (1.0 g, 1.24 mmol) was dissolved in pyridine (30 mL). MMTr-chloride (0.57 g, 1.86 mmol) was added and the reaction mixture was stirred at room temperature overnight. The mixture was evaporated to dryness and the residue was dissolved in $CH_2Cl_2$ and washed with saturated $NaHCO_3$. The organic phase was dried over $Na_2SO_4$, and evaporated to dryness. The product was purified by silica gel chromatography (petroleum ether/AcOEt v/v, 5/1→5/1→1/1 to yield 1.0 g (75%) of Compound 26. ESI-MS: $[M+H]^+$ 1074.28; calcd. for $C_{52}H_{61}Br_2N_5O_{10}^+$ 1074.27.

Example 27

The synthesis of 2,2',2",2'''-{[6-(methoxytrityl)oxy-hexylimino]bis(methylene)bis(4-(2,4,6-trimethoxyphenyl)pyridine-6,2-diyl)bis(methylenenitrilo)}tetrakis(acetic acid) tetra(methyl ester) 27

Reaction between Compound 27 and trimethoxyphenylboronic acid as described in Example 1 yielded the title compound. Yield was 97%. ESI-MS: $[M+H]^+$ 1250.66 calcd. for $C_{70}H_{84}N_5O_{16}^+$ 1250.59.

Example 28

The synthesis of 2,2',2",2'''-{[6-(hydroxyhexylimino]bis(methylene)bis(4-(2,4,6-trimethoxyphenyl)pyridine-6,2-diyl)bis(methylenenitrilo)}tetrakis(acetic acid) tetra(methyl ester) 28

Compound 27 (0.8 g, 0.64 mmol) was dissolved in 5% (v/v) solution of TFA in dichloromethane (16 mL) and the reaction mixture was stirred at room temperature for 3 hours. Methanol (10 mL) was added and the mixture was evaporated to dryness. The residue was dissolved in dichloromethane and was washed with saturated $NaHCO_3$ The organic phase was dried over $Na_2SO_4$ and evaporated to dryness. The product was purified by silica gel chromatography to yield 0.4 g (64%) of Compound 28. ESI-MS: $[M+H]^+$ 978.53 calcd. for $C_{50}H_{68}N_5O_{15}^+$ 978.46.

Example 29

Synthesis of the Phosphoramidite 29

Compound 28 (0.35 g, 0.36 mmol) was evaporated to dryness three times from dry acetonitrile and dissolved to the same solvent. 2-cyanoethyl tetraisopropylphosphor-diamidite (171 µL, 0.54 mmol) and tetrazole (0.45 M in acetonitrile; 800 µL, 0.36 mmol) were added and the reaction mixture was shaken at room temperature for 2 h. The reaction mixture was poured into saturated $NaHCO_3$ (5 mL) and the stirred vigorously. Dichloromethane was added, and the organic phase was dried over $Na_2SO_4$ and evaporated to dryness. The product was purified by silica gel chromatography (petroleum ether/AcOEt/triethylamine v/v/v, 2/5/1) to yield 0.20 g (47%) of Compound 29.

Example 30

The synthesis of 2,2',2",2'''-{[6-(hydroxyhexylimino]bis(methylene)bis(4-(2,4,6-trimethoxyphenyl)pyridine-6,2-diyl)bis(methylenenitrilo)}tetrakis(acetic acid) terbium (III) 30

Deprotection of compound 28 followed by treatment with terbium chloride as described in Example 20 yielded the title compound. ESI-MS: $[M+H]^+$ 1076.24; calcd. for $C_{46}H_{55}N_5O_{15}Tb^-$ 1076.30

Example 31

The synthesis of 2,2',2",2'''-{[6-(hydroxyhexylimino]bis(methylene)bis(4-(2,4,6-trimethoxyphenyl)pyridine-6,2-diyl)bis(methylenenitrilo)}tetrakis(acetic acid) dysprosium(III) 31

Deprotection of compound 28 followed by treatment with dysprosium chloride as described in Example 20 yielded the title compound. ESI-MS: $[M+H]^+$ 1081.31; calcd. for $C_{46}H_{55}N_5O_{15}Dy^-$ 1081.30.

Example 32

Synthesis of Oligopeptides on Solid Phase Using Block 4

Introduction of a lanthanide(III) chelate to the oligopeptide structure using compound 4 was performed using methods described in Peuralahti et al, *Bioconjugate Chem.*, 13, 2002, 870. Accordingly, the oligopeptide was synthesized in conventional manner, and the reactant 4 was coupled to amino terminus. Deprotection, conversion to the corresponding lanthanide(III) chelate and purification was performed as described.

Example 33

Synthesis of Oligonucleotides on Solid Phase Using Block 29

Introduction of a lanthanide(III) chelate to the oligonucleotide structure using compound 29 was performed using methods described in Hovinen and Hakala, *Org. Lett.* 3, 2001, 2473. Accordingly, the oligonucleotide was synthesized in conventional manner, and the reactant 50 was coupled to its 5'-terminus. Deprotection, convertion to the corresponding lanthanide(III) chelate and purification was performed as described.

Example 34

The synthesis of 9-[(trityloxy)methyl]-1,4,7-triazecane 1,4,7-tris-(2-nitrobenzenesulfonamide 32

2-((trityloxy)methyl)propane-1,3-diol (1.0 mmol), 2-nitrobenzenesulfonyl protected ethylene triamine (1.0 mmol) and triphenylphosphine (3.0 mmol) were dissolved in dry THF (5 mL). DIAD (3.0 mmol) was added in four portions during 15 min, and the reaction was allowed to proceed at room temperature overnight. All volatiles were removed in vacuo, and the residue was precipitated from diethyl ether. The precipitate was redissolved in dichloromethane, and the product was isolated on silica gel column (eluent 0.5% MeOH in $CH_2Cl_2$; v/v). ESI-MS: $[M+H]^+$ 971.21; calcd. for $C_{45}H_{43}N_6O_{13}S_3^+$ 971.20.

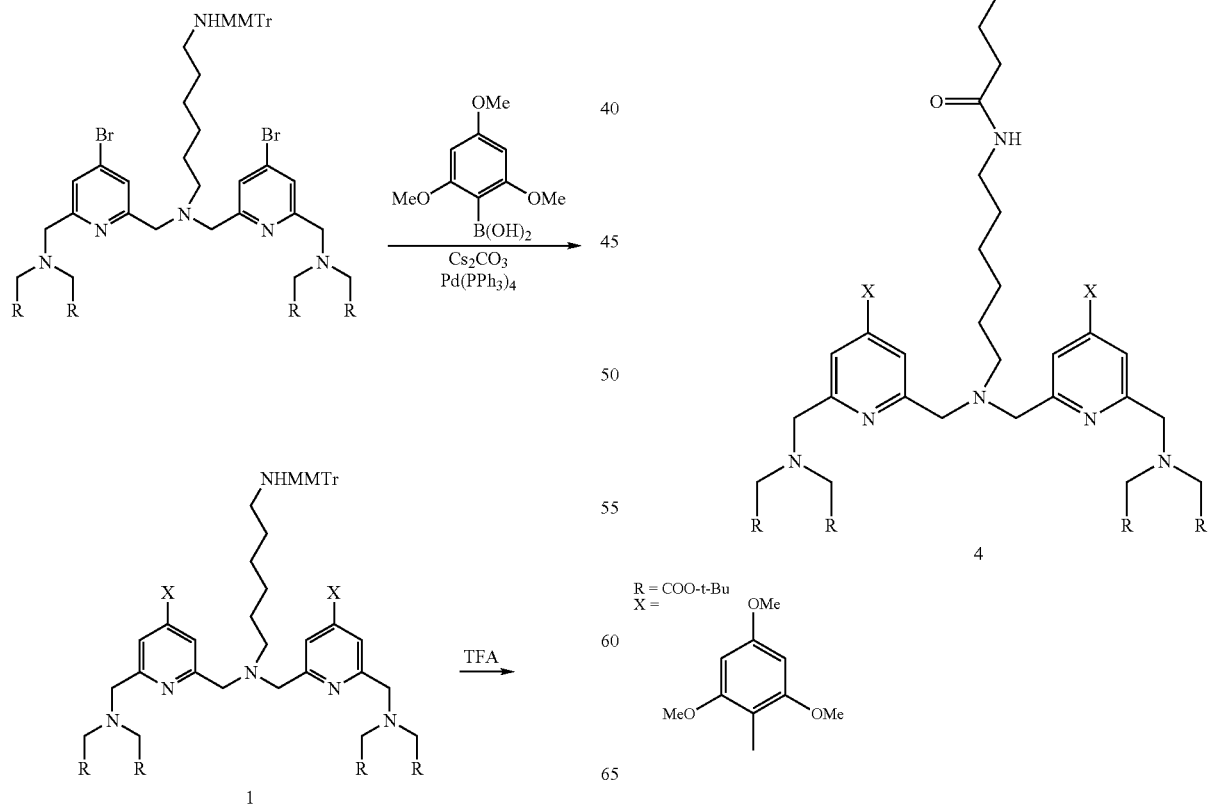

31
Scheme 2
32
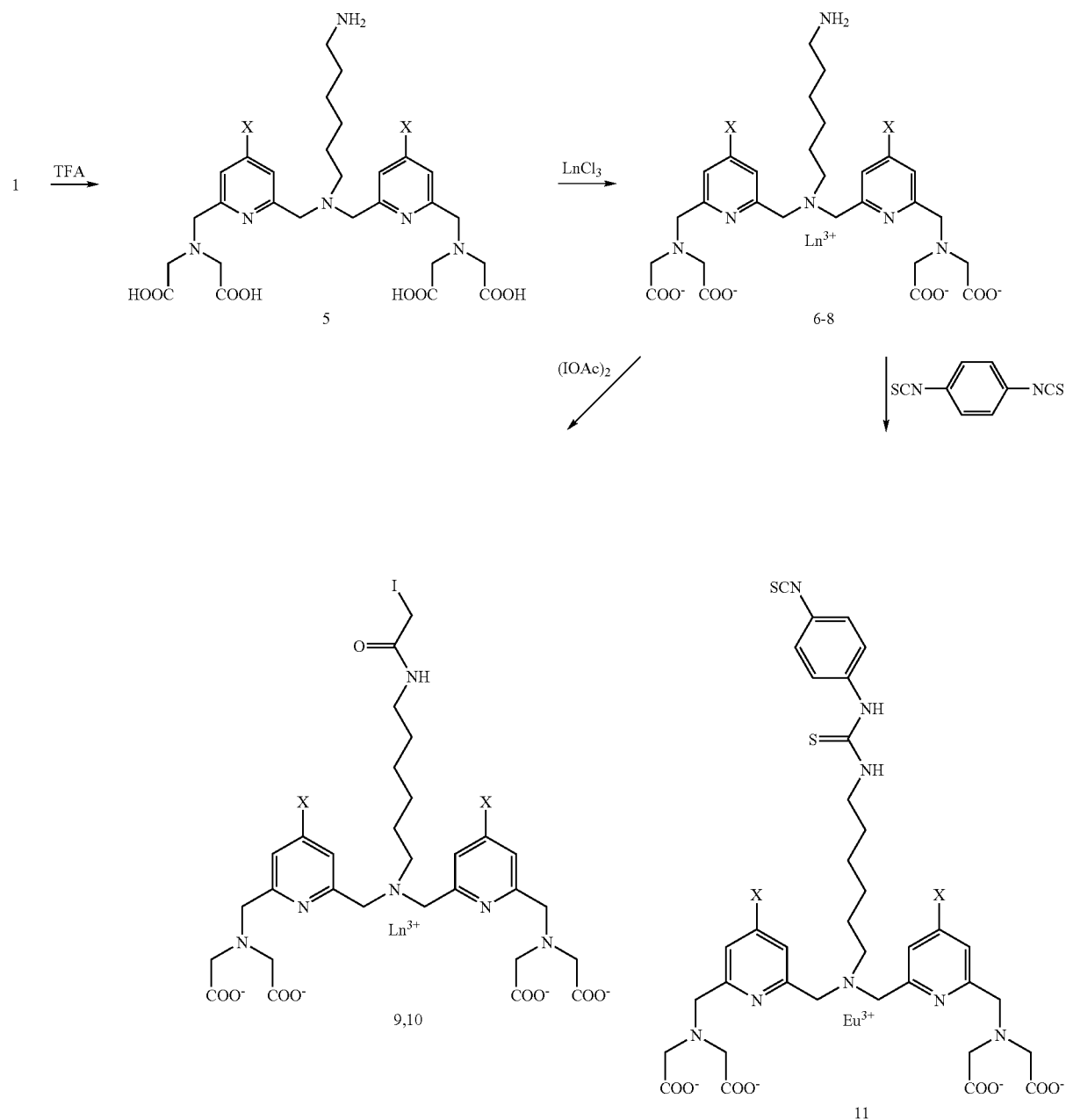
6, 10; Ln = Tb
7, 9; Ln = Dy
8; Ln = Eu
X =
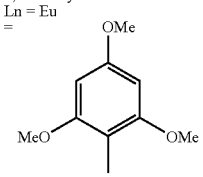

Scheme 3
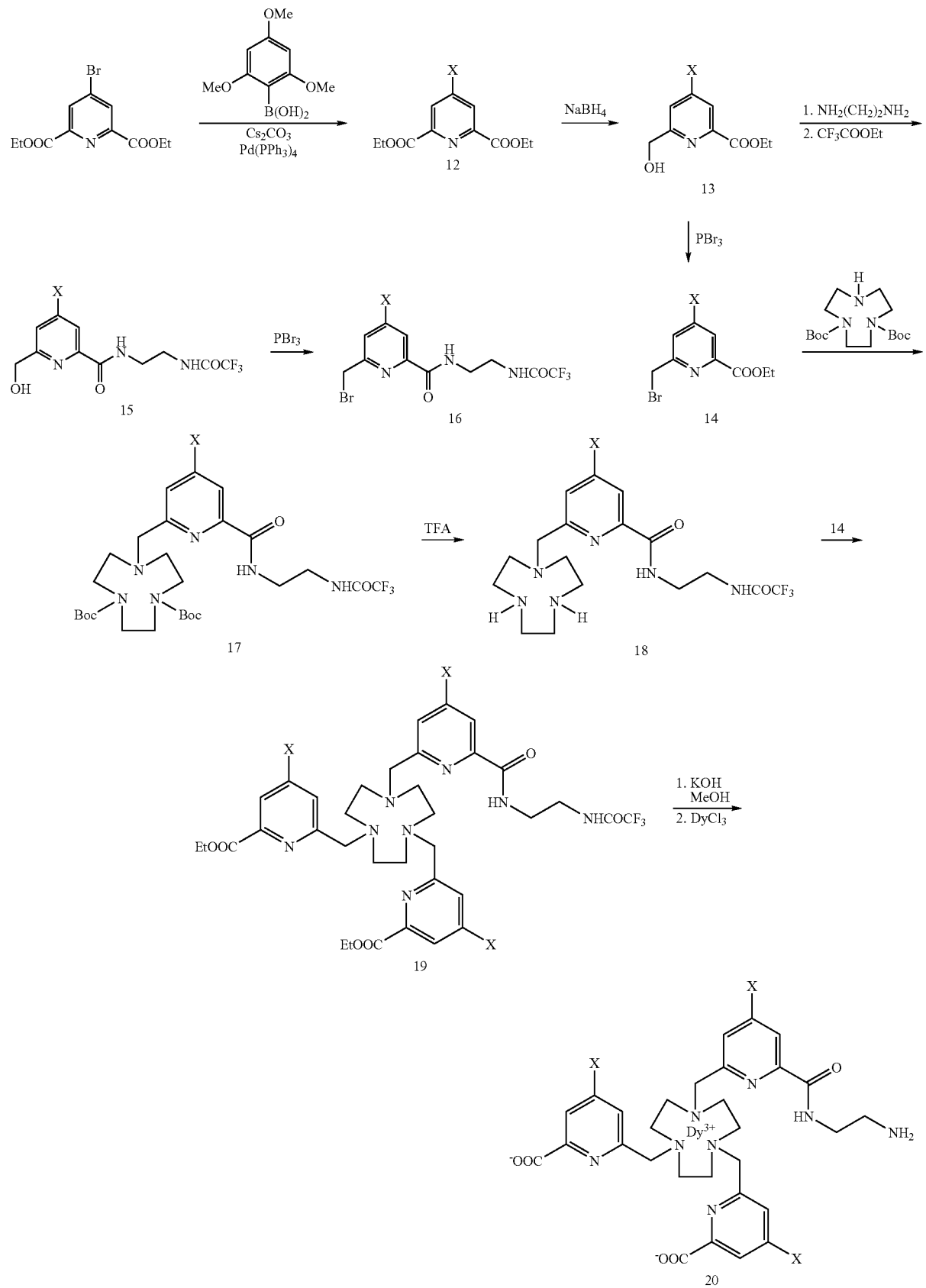

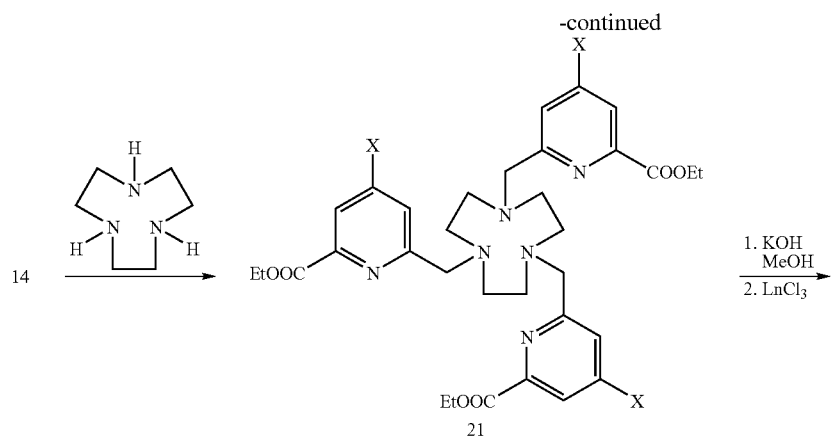
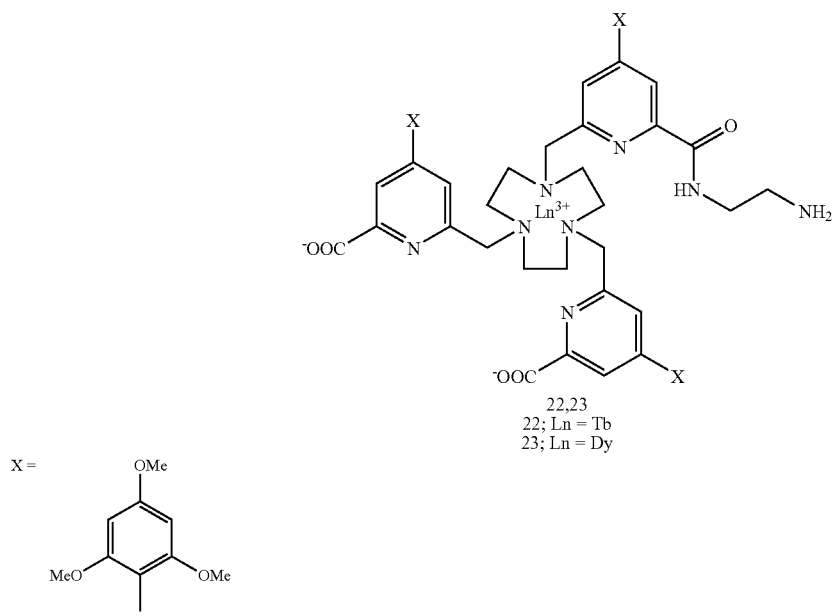
Scheme 4
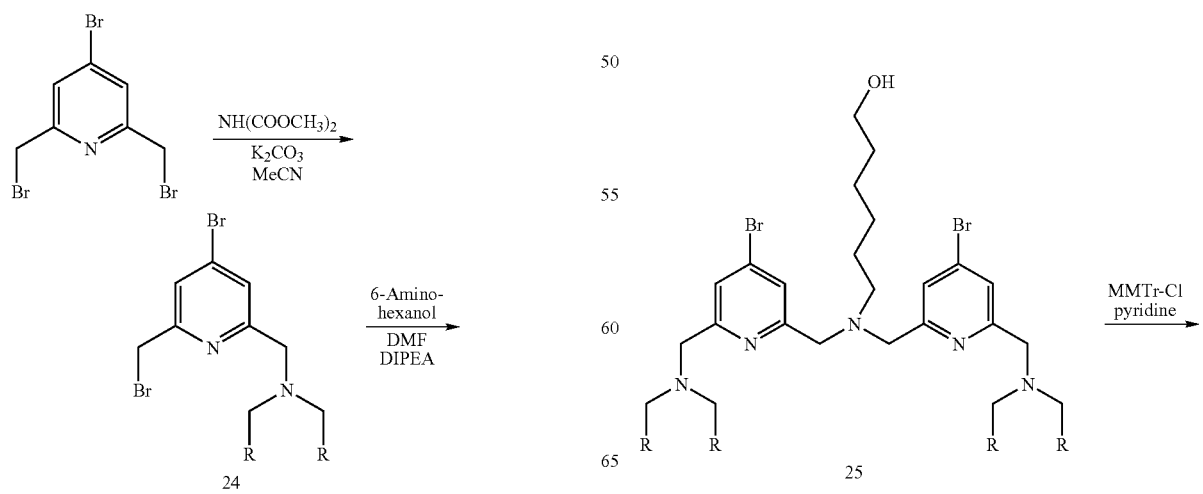

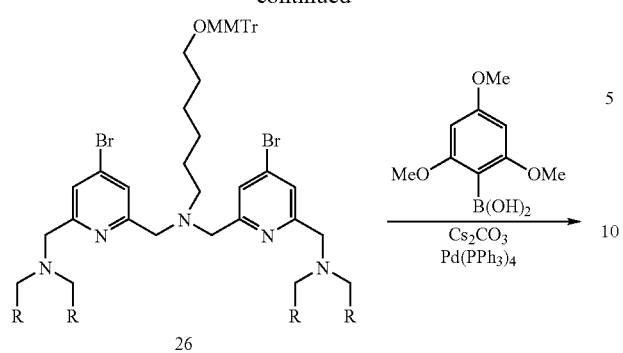
37
-continued
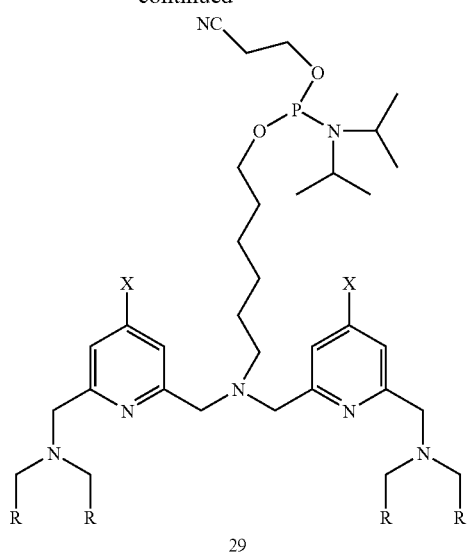
38
-continued
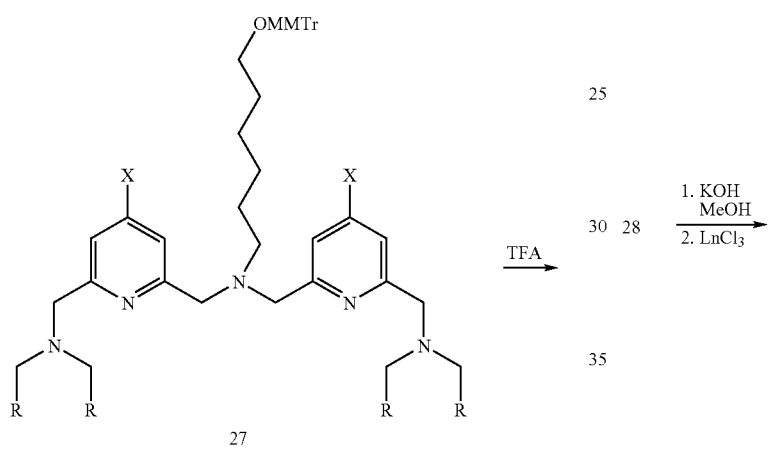
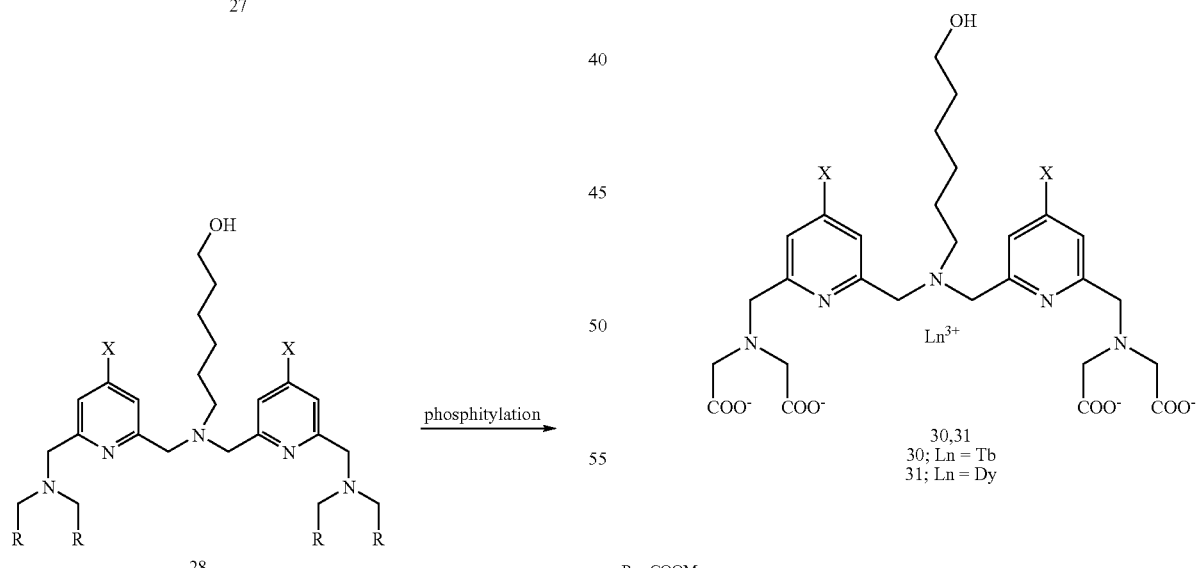
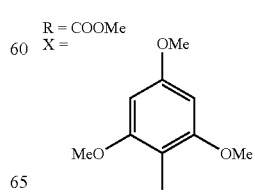

Scheme 5
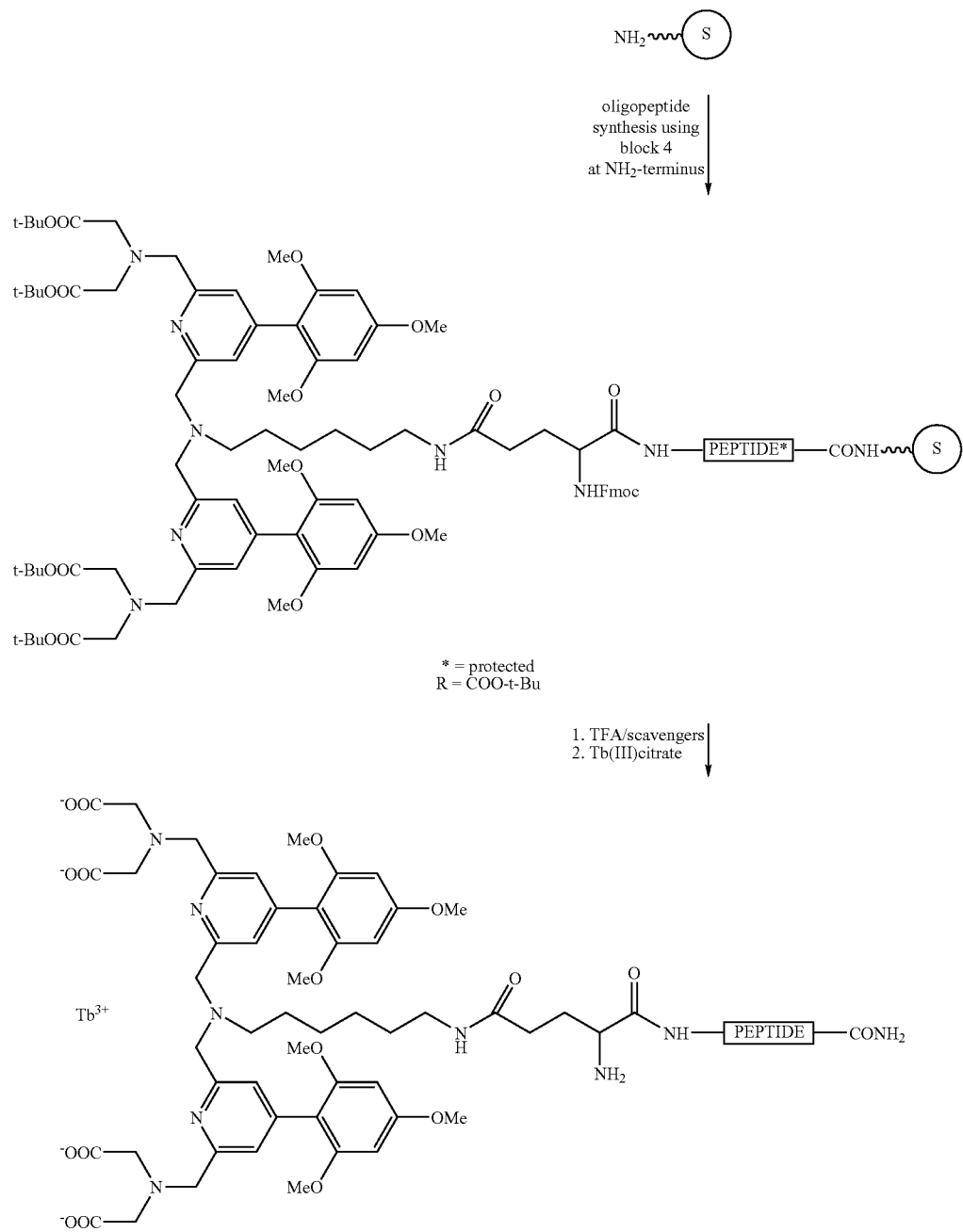
Scheme 6
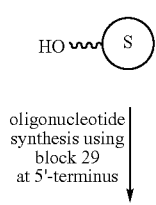

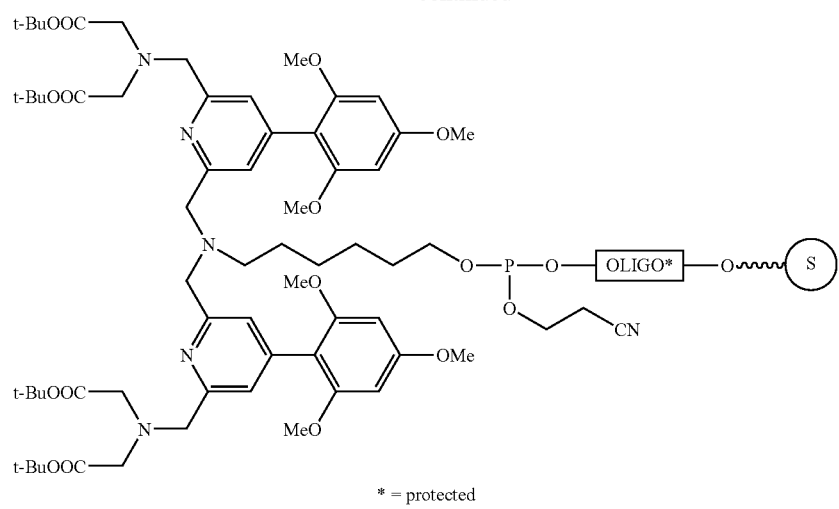
* = protected
1. oxidation
2. deprotection
3. treatment with Ln(III) citrate
Ln = Tb, Dy
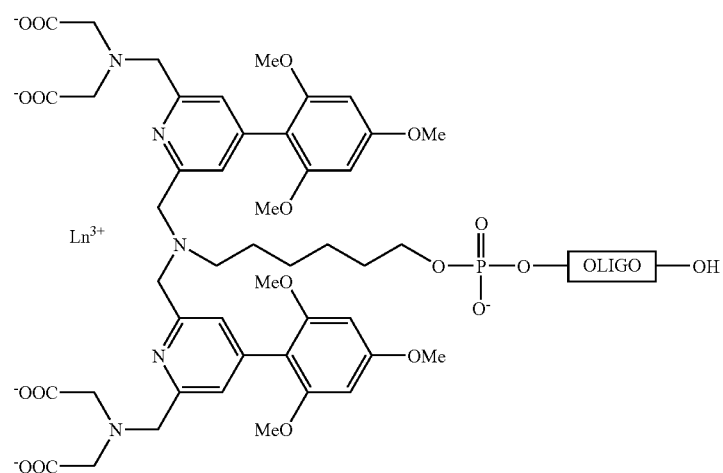
Scheme 7
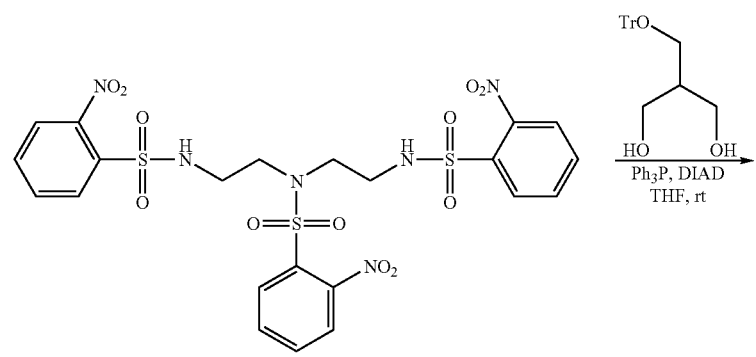

-continued
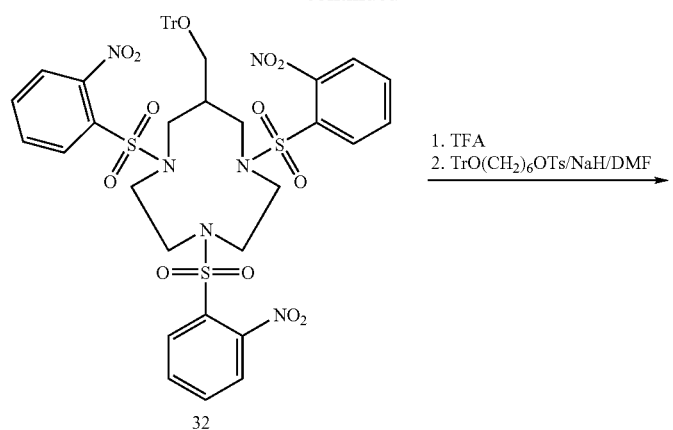
32
1. TFA
2. TrO(CH$_2$)$_6$OTs/NaH/DMF
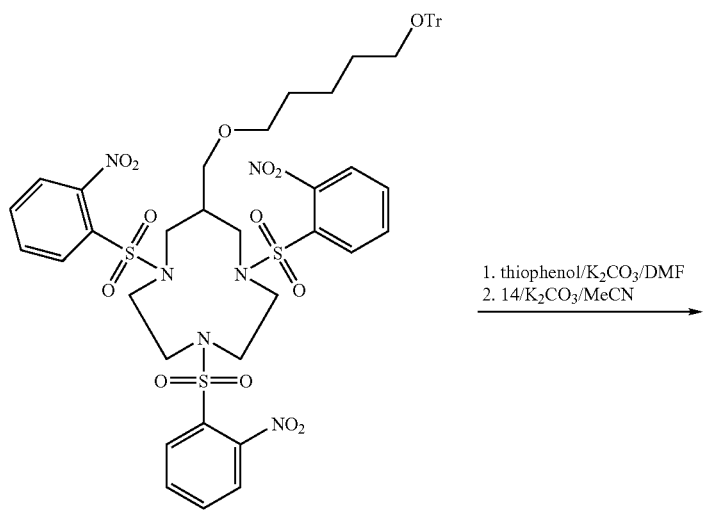
1. thiophenol/K$_2$CO$_3$/DMF
2. 14/K$_2$CO$_3$/MeCN
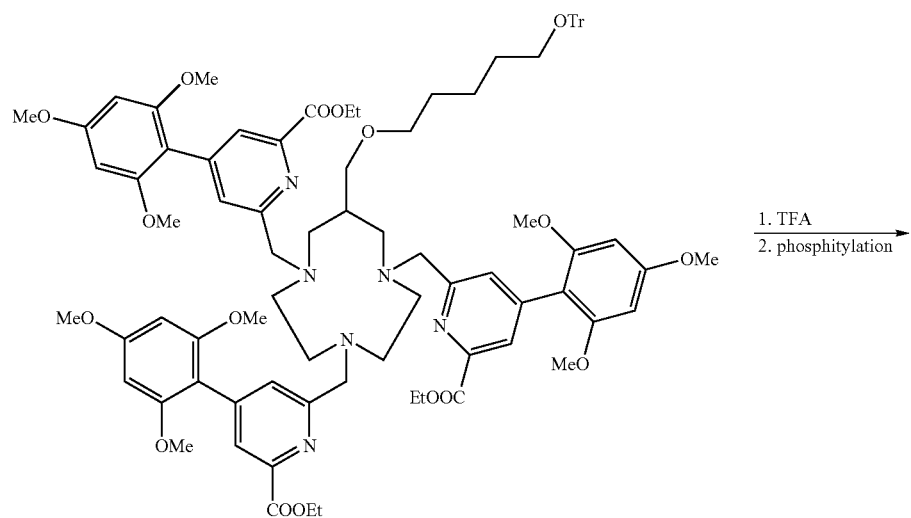
1. TFA
2. phosphitylation -continued
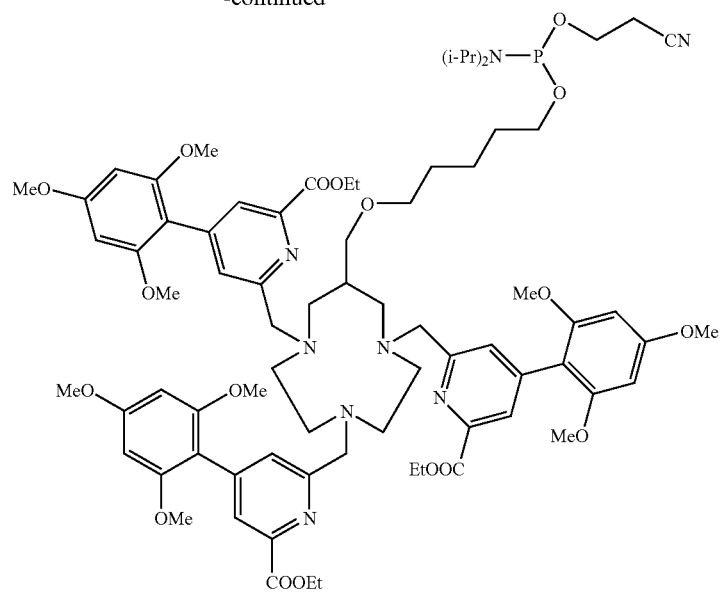
TABLE 1
Photochemical properties of some of the chelates synthesized
| Structure | Excitation max./nm | Emission max./nm | εΦ | Lifetime/ ms | Triplet state energy/cm$^{-1}$ |
|---|---|---|---|---|---|
| (structure 1) | 308 | 490<br>545<br>586<br>621 | 5389 | 1.98 | 22878 |
| (structure 2) | 303 | 490<br>545<br>586<br>621<br>649 | 7022 | 2.09 | |

TABLE 1-continued
Photochemical properties of some of the chelates synthesized
| Structure | Excitation max./nm | Emission max./nm | εΦ | Lifetime/ ms | Triplet state energy/cm$^{-1}$ |
|---|---|---|---|---|---|
| 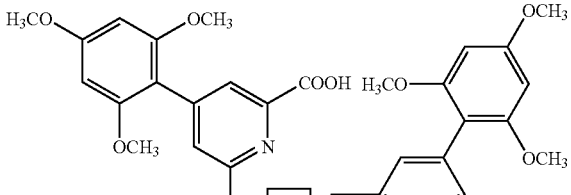 | 325 | 491<br>544<br>586<br>622<br>652<br>677 | | 1.21 | |
| 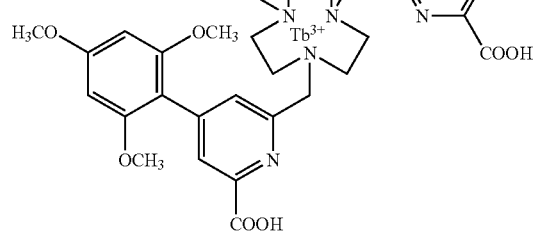 | 309 | 480<br>575<br>663<br>754 | 264 | 0.0199 | |
| 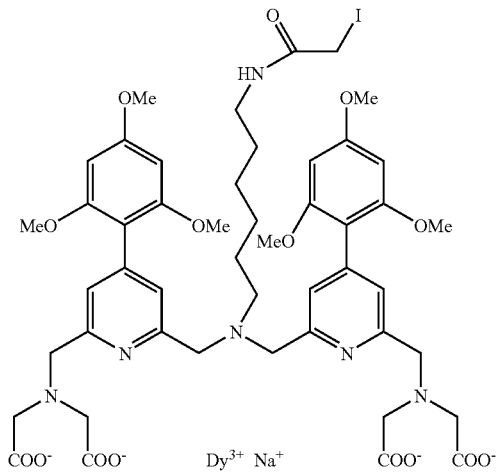 | 307 | 480<br>575<br>661<br>753 | 185 | 0.0203 | |

TABLE 1-continued

Photochemical properties of some of the chelates synthesized

| Structure | Excitation max./nm | Emission max./nm | εΦ | Lifetime/ ms | Triplet state energy/cm$^{-1}$ |
|---|---|---|---|---|---|
| 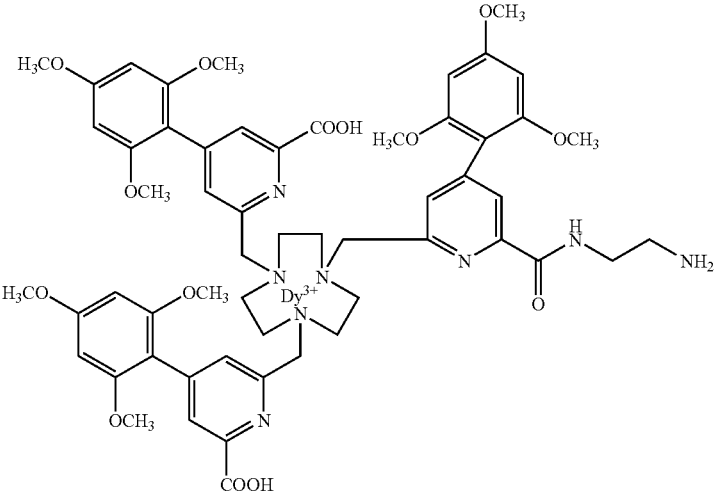 | 325 | 480<br>575<br>662<br>753 |  | 0.0145 |  |

The invention claimed is:

1. A chelate comprising:
   (a) a metal ion $M^{3+}$, wherein the metal is selected from a group consisting of europium, terbium, samarium and dysprosium;
   (b) two or more pyridyl groups, wherein at least one of said two or more pyridyl groups is substituted with a trialkoxyphenyl group, wherein the alkoxy groups are the same or different, and the pyridyl groups are i) tethered directly to each other to form a 2,2'-bipyridyl or 2,2':6',2''-terpyridyl group, respectively, or ii) tethered to each other via hydrocarbon chains, wherein said hydrocarbon chains contain no heteroatoms other than N;
   (c) at least two carboxylic acid or phosphonic acid groups, or esters or salts of said acid groups, attached to the pyridyl groups at ortho position either directly or via a hydrocarbon chain, wherein said hydrocarbon chain contains no heteroatoms other than N; and optionally
   (d) a substituent A selected from the group consisting of isothiocyanate, haloacetamido, maleimido, dichlorotriazinylamino, pyridyldithio, thioester, aminooxy, hydrazide, amino, a polymerizing group, a carboxylic acid or acid halide or an active ester thereof; wherein:
   said substituent A is tethered to i) at least one of said two or more pyridyl groups, or ii) at least one of said hydrocarbon chains, either directly or via a linker x, wherein said linker x is formed from one to ten moieties, each moiety being selected from the group consisting of phenylene, alkylene containing 1-12 carbon atoms, ethynydiyl (—C≡C—), ethylenediyl (—C=C—), ether (—O—), thioether (—S—) amide (—CO—NH—, —CO—NR'—, NH—CO— and —NR'—CO—), carbonyl (—CO—), ester (—COO— and —OOC—), disulfide (—SS—), diaza (—N=N—), and tertiary amine, wherein R' represents an alkyl group containing less than 5 carbon atoms.

2. The chelate according to claim 1, wherein said two or more pyridyl groups are tethered to each other via hydrocarbon chains, wherein said hydrocarbon chains contain no heteroatoms other than N.

3. The chelate according to claim 1 selected from a group consisting of

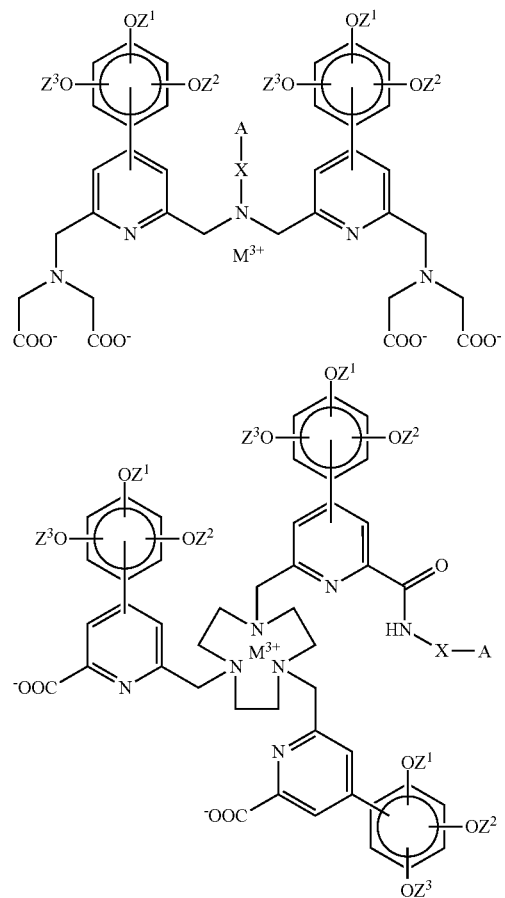

51
-continued
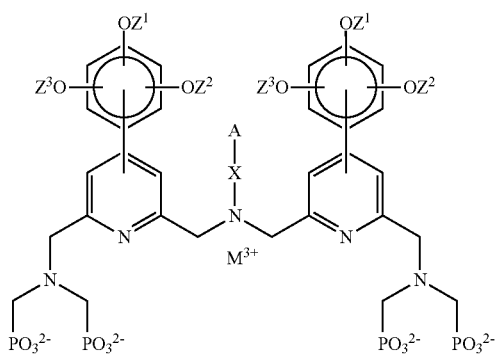
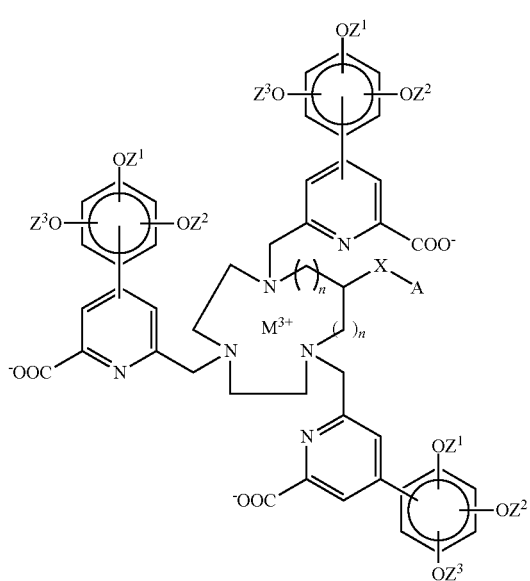
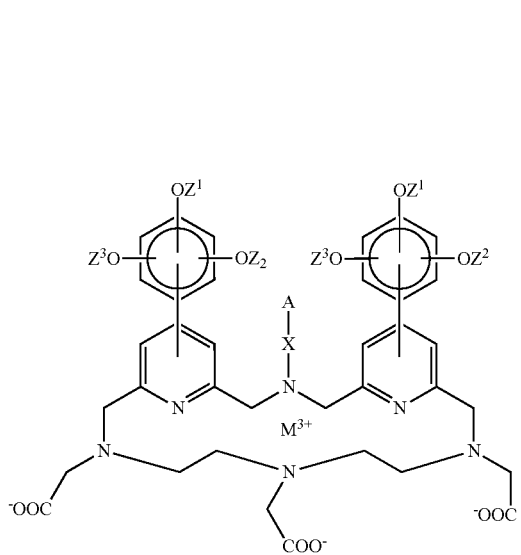
52
-continued
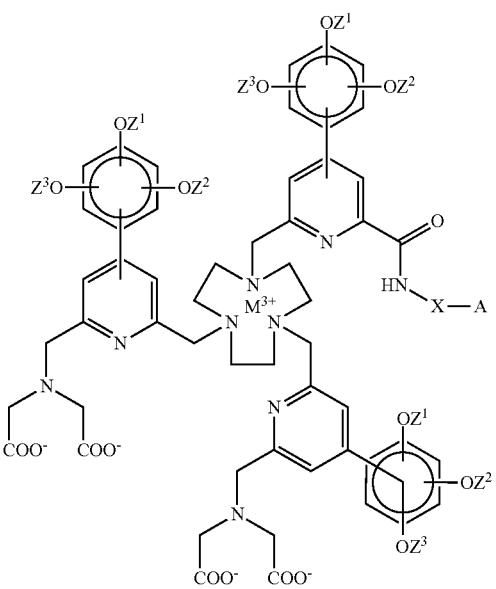
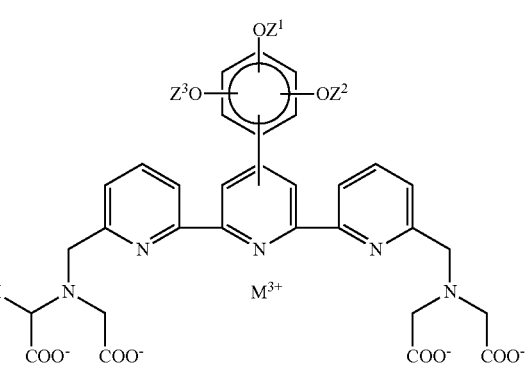
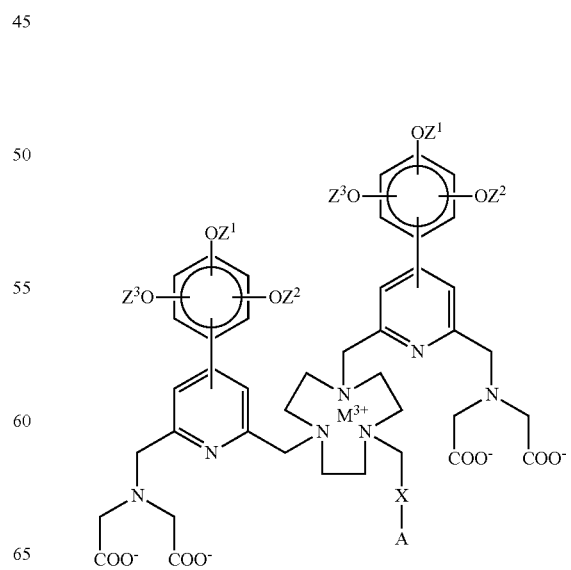

-continued
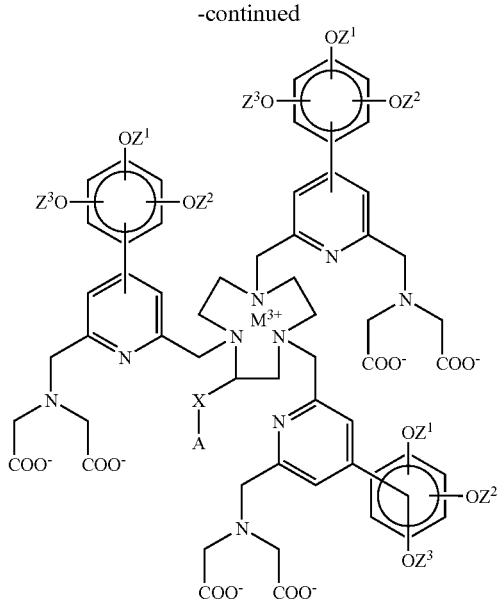
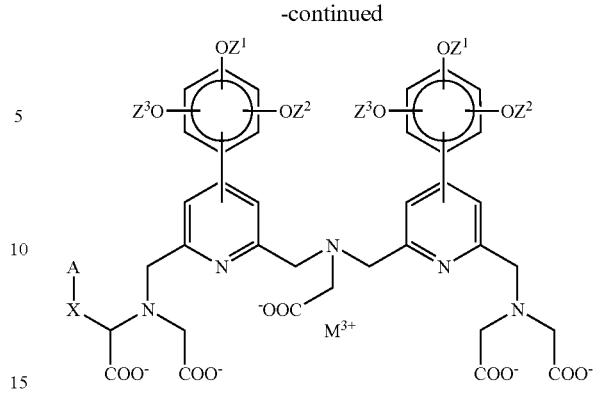
wherein Z1, Z2 and Z3 are the same or different alkyl groups.
* * * * *